(12) United States Patent
Diao et al.

US009387468B2

(10) Patent No.: US 9,387,468 B2
(45) Date of Patent: Jul. 12, 2016

(54) COBALT CATALYSTS AND THEIR USE FOR HYDROSILYLATION AND DEHYDROGENATIVE SILYLATION

(71) Applicants: Tianning Diao, New York, NY (US); Paul J. Chirik, Princeton, NJ (US); Aroop Kumar Roy, Mechanicville, NY (US); Kenrick Lewis, Flushing, NY (US); Susan Nye, Feura Bush, NY (US); Keith J. Weller, Rensselaer, NY (US); Johannes G. P. Delis, Bergen op Zoom (NL); Renyuan Yu, Beijing (CN)

(72) Inventors: Tianning Diao, New York, NY (US); Paul J. Chirik, Princeton, NJ (US); Aroop Kumar Roy, Mechanicville, NY (US); Kenrick Lewis, Flushing, NY (US); Susan Nye, Feura Bush, NY (US); Keith J. Weller, Rensselaer, NY (US); Johannes G. P. Delis, Bergen op Zoom (NL); Renyuan Yu, Beijing (CN)

(73) Assignees: Momentive Performance Materials Inc., Waterford, NY (US); Princeton University, Princeton, NJ (US)

( * ) Notice: Subject to any disclaimer, the term of this patent is extended or adjusted under 35 U.S.C. 154(b) by 0 days.

(21) Appl. No.: 14/547,641

(22) Filed: Nov. 19, 2014

(65) Prior Publication Data
US 2015/0137033 A1 May 21, 2015

Related U.S. Application Data

(60) Provisional application No. 61/906,210, filed on Nov. 19, 2013.

(51) Int. Cl.
| | | |
|---|---|---|
| *C07F 15/06* | (2006.01) | |
| *B01J 21/06* | (2006.01) | |
| *C07F 7/18* | (2006.01) | |
| *B01J 31/22* | (2006.01) | |
| *C08G 81/02* | (2006.01) | |
| *C07F 7/08* | (2006.01) | |

(52) U.S. Cl.
CPC ........... *B01J 31/2295* (2013.01); *C07F 7/0856* (2013.01); *C07F 7/0879* (2013.01); *C07F 7/184* (2013.01); *C07F 7/1836* (2013.01); *C07F 7/1876* (2013.01); *C07F 15/06* (2013.01); *C07F 15/065* (2013.01); *C08G 81/02* (2013.01); *B01J 2231/14* (2013.01); *B01J 2231/323* (2013.01); *B01J 2231/766* (2013.01); *B01J 2531/845* (2013.01)

(58) Field of Classification Search
USPC .............................. 546/2, 14; 502/260; 556/9
See application file for complete search history.

(56) References Cited

U.S. PATENT DOCUMENTS

| | | | |
|---|---|---|---|
| 3,159,601 | A | 12/1964 | Ashby et al. |
| 3,220,972 | A | 11/1965 | Lamoreaux |
| 3,296,291 | A | 1/1967 | Chalk et al. |
| 3,775,452 | A | 11/1973 | Karstedt |
| 3,928,629 | A | 12/1975 | Chandra et al. |
| 4,550,152 | A | 10/1985 | Faltynek |
| 4,572,791 | A | 2/1986 | Onopchenko et al. |
| 4,572,971 | A | 2/1986 | Necoechea |
| 4,578,497 | A | 3/1986 | Onopchenko et al. |
| 4,729,821 | A | 3/1988 | Timmons et al. |
| 4,788,312 | A | 11/1988 | Paciorek et al. |
| 5,026,893 | A | 6/1991 | Paciorek |
| 5,166,298 | A | 11/1992 | Friedman et al. |
| 5,331,075 | A | 7/1994 | Sumpter et al. |
| 5,432,140 | A | 7/1995 | Sumpter et al. |
| 5,866,663 | A | 2/1999 | Brookhart et al. |
| 5,955,555 | A | 9/1999 | Bennett |
| 6,103,946 | A | 8/2000 | Brookhart et al. |
| 6,214,761 | B1 | 4/2001 | Bennett |
| 6,265,497 | B1 | 7/2001 | Herzig |
| 6,278,011 | B1 | 8/2001 | Chen et al. |
| 6,281,303 | B1 | 8/2001 | Lavoie et al. |
| 6,297,338 | B1 | 10/2001 | Cotts et al. |
| 6,417,305 | B2 | 7/2002 | Bennett |
| 6,423,848 | B2 | 7/2002 | Bennett |
| 6,432,862 | B1 | 8/2002 | Bennett |
| 6,451,939 | B1 | 9/2002 | Britovsek |
| 6,455,660 | B1 | 9/2002 | Clutton et al. |
| 6,458,739 | B1 | 10/2002 | Kimberley et al. |
| 6,458,905 | B1 | 10/2002 | Schmidt et al. |
| 6,461,994 | B1 | 10/2002 | Gibson et al. |
| 6,472,341 | B1 | 10/2002 | Kimberley et al. |
| 6,620,895 | B1 | 9/2003 | Cotts et al. |
| 6,657,026 | B1 | 12/2003 | Kimberley et al. |
| 7,053,020 | B2 | 5/2006 | De Boer et al. |
| 7,148,304 | B2 | 12/2006 | Kimberley et al. |
| 7,161,005 | B2 | 1/2007 | Schlingloff et al. |
| 7,247,687 | B2 | 7/2007 | Cherkasov et al. |

(Continued)

FOREIGN PATENT DOCUMENTS

| | | |
|---|---|---|
| CN | 1727349 | 2/2006 |
| EP | 0786463 | 7/1997 |

(Continued)

OTHER PUBLICATIONS

Archer et al., "Arene Coordination in Bis(imino)pyridine Iron Complexes: Identification of Catalyst Deactivation Pathways in Iron-Catalyzed Hydrogenation and Hydrosilation," Organometallics, vol. 25, pp. 4269-4278 (2006).

(Continued)

*Primary Examiner* — Charanjit Aulakh
(74) *Attorney, Agent, or Firm* — Joseph E. Waters; McDonald Hopkins LLC

(57) ABSTRACT

Disclosed herein are cobalt complexes containing pyridine di-imine ligands and chelating alkenyl-modified silyl ligands, and their use as hydrosilylation and/or dehydrogenative silylation and crosslinking catalysts. The cobalt complexes also exhibit adequate air stability for handling and manipulation.

49 Claims, No Drawings

(56) References Cited

U.S. PATENT DOCUMENTS

| | | | |
|---|---|---|---|
| 7,268,096 B2 | 9/2007 | Small et al. | |
| 7,429,672 B2 | 9/2008 | Lewis et al. | |
| 7,442,819 B2 | 10/2008 | Ionkin et al. | |
| 7,456,285 B2 | 11/2008 | Schlingloff et al. | |
| 7,696,269 B2 | 4/2010 | Cruse et al. | |
| 8,236,915 B2 | 8/2012 | Delis et al. | |
| 8,415,443 B2 | 4/2013 | Delis et al. | |
| 8,895,770 B2 * | 11/2014 | Lewis et al. | 556/456 |
| 2002/0058584 A1 | 5/2002 | Bennett | |
| 2006/0263675 A1 | 11/2006 | Adzic et al. | |
| 2007/0264189 A1 | 11/2007 | Adzic et al. | |
| 2008/0262225 A1 | 10/2008 | Schlingloff et al. | |
| 2008/0293878 A1 | 11/2008 | Funk et al. | |
| 2009/0068282 A1 | 3/2009 | Schlingloff et al. | |
| 2009/0296195 A1 | 12/2009 | Fontana et al. | |
| 2011/0009565 A1 | 1/2011 | Delis et al. | |
| 2011/0009573 A1 | 1/2011 | Delis et al. | |
| 2012/0130021 A1 | 5/2012 | Tondreau et al. | |
| 2012/0130105 A1 | 5/2012 | Lewis et al. | |
| 2012/0130106 A1 | 5/2012 | Chirik et al. | |
| 2013/0158281 A1 | 6/2013 | Weller et al. | |
| 2014/0051822 A1 | 2/2014 | Atienza et al. | |
| 2014/0243486 A1 | 8/2014 | Roy et al. | |
| 2014/0330024 A1 | 11/2014 | Atienza et al. | |
| 2014/0330036 A1 | 11/2014 | Lewis et al. | |
| 2014/0343311 A1 | 11/2014 | Boyer et al. | |
| 2015/0080536 A1 | 3/2015 | Diao et al. | |

FOREIGN PATENT DOCUMENTS

| | | |
|---|---|---|
| GB | 2013207 | 8/1979 |
| TW | 200902541 | 1/2009 |
| WO | 9210544 | 6/1992 |
| WO | 02088289 | 11/2002 |
| WO | 03042131 | 5/2003 |
| WO | 2008085453 | 7/2008 |
| WO | 2011006044 | 1/2011 |
| WO | 2012071359 | 5/2012 |
| WO | 2013/043783 | 3/2013 |
| WO | 2013/043846 | 3/2013 |
| WO | 2013043846 | 3/2013 |
| WO | 2015/023328 | 2/2015 |

OTHER PUBLICATIONS

Bowman et al., "Reduced N-Alkyl Substituted Bis(imino)pyridine Cobalt Complexes: Molecular and Electronic Structures for Compounds Varying by Three Oxidation States," Inorg. Chem. 2010, 49, 6110-6123, Germany.

Zhu et al., A Measure for *-Donor and *-Acceptor Properties of Diiminepyridine-Type Ligands, Organometallics 2008, 27, 2699-2705.

International Preliminary Report on Patentability for PCT/US2010/041487 dated Jan. 19, 2012.

Bart et al., "Electronic Structure of Bis(imino)pyridine Iron Dichloride, Monochloride, and Neutral Ligand Complexes: A Combined Structural, Spectroscopic, and Computational Study," J. Am. Chem. Soc. 2006, 128, 13901-13912.

Bart et al., "Preparation and Molecular and Electronic Structures of Iron(0) Dinitrogen and Silane Complexes and Their Application to Catalytic Hydrogenation and Hydrosilation," Journal of the American Chemical Society, vol. 126, pp. 13794-13807 (2004).

Connelly et al., "Chemical Redox Agents for Organometallic Chemistry," Chem. Rev. 1996, 96, 877-910.

Atienza et al. "Synthesis, Electronic Structure, and Ethylene Polymerization Activity of Bis(imino)pyridine Cobalt Alkyl Cations," Agnewandte Chem. Int. Ed. 2011, 50, 8143-8147.

Glatz et al., "Terpyridine-Based Silica Supports Prepared by Ring-Opening Metathesis Polymerization for the Selective Extraction of Noble Metals," Journal of Chromatography A, vol. 1015, pp. 65-71 (2003).

Nagashima et al., "Dehydrogenative Silylation of Ketones with a Bifunctional Organosilane by Rhodium- Pybox Catalysts," Chem. Soc. of Jpn., Chemistry Letters, 1993, 347-350, Toyohashi, Aichi 441.

Hosokawa et al., A Chiral Iron Complex Containing a Bis(oxazolinyl)phenyl Ligand: Preparation and Asymmetric Hydrosilylation of Ketones. Organometallics, 29, 5773-5775 (2010).

Kaul et al., Immobilization of Bis(imino)pyridyliron (II) complexes on Silica, Organometallics, 2002, 21(1), 74-83.

Kim et al., "2,2':6',2"-Terpyridine and Bis(2,2':6',2"-terpyridine)Ruthenium(II) Complex on the Dendritic Periphery," Journal of Organometallic Chemistry, vol. 673, pp. 77-83 (2003).

Kroll et al., "Access to Heterogeneous Atom-Transfer Radical Polymerization (ATRP) Catalysts Based on Dipyridylamine and Terpyridine via Ring-Opening Metathesis Polymerization (ROMP)," Macromolecular Chemistry and Physics, vol. 202, pp. 645-653 (2001).

Field et al., One-Pot Tandem Hydroamination/Hydrosilation Catalyzed by Cationic Iridium(I) Complexes, Organometallics, vol. 22, pp. 4393-4395, Sep. 25, 2003.

Dekamin et al., "Organocatalytic, rapid and facile cyclotrimerization of isocyanates using tetrabutylammonium phthalimide-N-oxyl and tetraethylammonium 2-(carbamoyl) benzoate under solvent-free conditions," Catalysis Communications 12 (2010) 226-230.

Nesmeyanov et al., "Addition, Substitution, and Telomerization Reactions of Olefins in the Presence of Metal Carbonyls or Colloidal Iron," Tetrahedron, vol. 17, pp. 61-68 (1962).

Pal, et al., Preparation and hydrosilylation activity of a molybdenum carbonyl complex that features a pentadentate bis(amino)pyridine lignad. Inorg Chem. Sep. 2, 2014; 53(17):9357-65. doi: 10.1021/ic501465v. Epub Aug. 20, 2014.

Jairam et al., "Ester Hydrolysis with 2,6-di(pyrazol-3-yl)pyridines and their Co 11 Complexes in Homogeneous and Micellar Media," Journal of Inorganic Biochemistry 84, 2001, 113-118, Toronto, Ontario, Canada.

Buschbeck et al., Triethylene Glycol Ether End-grafted Carbosilane Dendrimers: Synthesis and Complexation Behavior, Inorganic Chemistry Communications, vol. 7, pp. 1213-1216, Oct. 13, 2004.

Seckin, Preparation and Catalytic Properties of a Ru(II) Coordinated Polyimide Supported by a Ligand Containing Terpyridine Units, Journal of Inorganic and Organometallic Polymers and Materials, Apr. 9, 2009, 19(2), 143-151.

Sieh et al., Metal-Ligand Electron Transfer in 4d and 5d Group 9 Transition Metal Complexes with Pyridine, Diimine Ligands. Eur. J. Inorg. Chem., 2012:444-462. doi 10.1002/ejic.201101072.

Speier et al., "The Addition of Silicon Hydrides to Olefinic Double Bonds. Part II. The Use of Group VIII Metal Catalysts," Journal of the American Chemical Society, vol. 79, pp. 974-979 (1956).

Thammavongsy et al., Ligand-Based Reduction of CO2 and Release of CO and Iron(II). Inorg. Chem., 2012, 51 (17), pp. 9168-9170. DOI: 10:1021/ic3015404. Publication Date (Web): Aug. 20, 2012.

Timpa, "Non-Innocent Pyridine Based Pincer Ligands and Their Role Catalysis" dated Nov. 1, 2010.

International Preliminary Report on Patentability for PCT/US2011/061746 dated Jun. 6, 2013.

Tondreau, et al "Synthesis and electronic structure of cationic, neutral, and anionic bis(imino)pyridine iron alkyl complexes: evaluation of redox activity in single-component ethylene polymerization catalysts." J Am Chem Soc. Oct. 27, 2010; 132(42): 15046-59. doi: 10.1021/ja106575b.

Gibson et al., "The nature of the active species in bis(imino)pyridyl cobalt ethylene polymerisation catalysts," Chem. Commun., 2001, 2252-2253.

Wile, et al. "Reduction chemistry of aryl- and alkyl-substituted bis(imino)pyridine iron dihalide compounds: molecular and electronic structures of [(PDI)2Fe] derivatives." Inorg Chem May 4, 2009; 48(9):4190-200.

International Preliminary Report on Patentability for PCT/US2012/069469 dated Mar. 12, 2014.

International Preliminary Report on Patentability for PCT/US2011/061752 dated May 28, 2013.

Abu-Surrah et al., Journal of Organometallic Chemistry 648 (2002) 55-61.

(56) References Cited

OTHER PUBLICATIONS

Albon et al., "Metal Carbonyl Complexes Involving 2,6Bix[I-(phenylimino)ethyl]pyridine; Bidentate Corrdination of a Potentially Tridentate Ligand" Inorganica Chimica Acta, 159 (1989) 19-22.

Alyea et al., Syn. React. Inorg. Metal-Org. Chem., 4(6), 535-544 (1974).

Bouwkamp M W, Iron-Catalyzed [$2\pi+2\pi$] Cycloaddition of $\alpha,\omega$-Dienes the Importance of Redox-Active Supporting Ligands, Journal of the Americal Chemical Society, 2006, V128 N41, P13340-13341.

Britovsek et al., "Novel Olefin Polymerization Catalysts Based on Iron and Cobalt," Chem. Commun., 1998, 849-850.

Cetinkaya et al., Journal of Molecular Catalysis A: Chemical 142 (1999) 101-112.

Chen et al., "General Synthesis of Di-u-oxo Dimanganese Complexes as Functional Models for the Oxygen Evolving Complex of Photosystem II" Inorg. Chem. 2005, 44, 7661-7670.

Corey, Joyce Y. et al., "Reactions of Hydrosilanes with Transition-Metal Complexes: Formation of Stable Transition-Metal Silyl Compounds," Journal of Chemical Reviews, vol. 99, pp. 175-292 (1999).

Fernandez et al., "Synthesis and Reactions of Dihydrido(triethylalyl)(1,5-cycloctadiene)-Iridium(III) Complexes: Catalysts for Dehydrogneative Silylation of Alkenese," Organometallics, 1986, 5, 1519-1520.

Haarman et al., "Reactions of [RhCI(diene)]2 with Bi- and Terdentate Nitrogen Ligands. X-ray Structures of Five-Coordinate Complexes," Am. Chem. Soc., Organometallics 1997, 16, 54-67.

Humphries et al., "Investigations into the Mechanism of Activation and Initiation of Ethylene Polymerization by Bis(imino)pyridine Cobalt Catalysts: Synthesis, Structures, and Deuterium Labeling Studies," Organometallics 2005, 24, 2039-2050, London, United Kingdom.

Kakiuchi et al., "Completely Selective Synthesis of (E)-B-(triethylsilyl)styrenes by Fe3(CO)12-catalyzed Reaction of Styrenes With Triethylsilane," Journal of Organometallic Chemistry 1993, 456, 45-47, Osaka, Japan.

Kakiuchi et al., "Dehydrogenative Silylation of 1,5-Dienes with Hydrosilanes Catalyzed by RhCI (PPh3)3," Am. Chem. Soc., Organometallics, 1993, 12, 4748-4750, Kagawa, Japan.

Kickelbick et al., New J. Chem., 2002, 26, 462-468.

Kooistra et al., Inorganica Chimica Acta 357 (2004) 2945-2952.

Kuo, et al., "Electrochemical studies of nickel bis(2,2':6',2"-terpyridine) with alkyl/aryl/allyl bromides and activeated olefins in nonaqueous solvents" Jiemian Kexue Huishi, vol. 15, Issue 1, pp. 23-42, Journal, 1992.

Lapointe, et al., "Mechanistic Studies of Palladium(II)-Catalyzed Hydrosiliation and Dehydrogenative Silation Reactions," J. Amer. Chem. Soc. 119 (1997), pp. 906-917.

Lewis et al., "Hydrosilylation Catalized by Metal Colloids: A Relative Activity Study," Organometallics, 9 (1990), 621-625.

Lions et al., J. Chem. Soc. (A) 1957, vol. 79, 2733-2738.

Lu et al., "Iridium-Catalyzed (Z)-Trialkylsilylation ofTerminal Olefins," J. Org. Chem, 2010, 75, 1701-1705, Dallas, Texas.

Lu et al., "The Molecular Structure of a Complex of a 2,6-Diimino-Pyridine as a Bidentate Lignad with Molybdenum Carbonyl" Inorganica Chimica Acta, 134 (1987) 229-232.

Marciniec et al., "Competitve silylation of olefins with vinylsilanes and hydrosilanes photocatalyzed by iron carbonyl complexes," Inorg. Chem. Commun. 2000, 3, 371.

McAtee et al., "Preparation of Allyl and Vinyl Silanes by the Palladium-Catalyzed Silylation of Terminal Olefins: A Silyl-Heck Reaction**," Angewandte Chemie, Int. Ed. 2012, 51, 3663-3667.

Naumov et al., "Selective Dehydrogentative Silylation-Hydrogenation Reaction of Divinyldisiloxane with Hydrosilane Catalyzed by an Iron Complex," Journal of the American Chemical Society, 2012, vol. 134, Issue 2, 804-807, Osaka, Japan.

Oro, L. A., et al. "Hydrosilylation of Alkenese by Iridium Complexes," J. Mol. Catalysis, 1986, 37, 151-156.

Pangborn, et al., "Safe and Convenient Procedure for Solvent Purification," Oraganometallics, 15:1518 (1996).

Randolph, Claudia L. et al., "Photochemical Reactions of ($\eta$5-Pentamethylcyclopentadienyl)dicarbonyliron-Alkyl and Silyl Complexes: Reversible Ethylene Insertion into an Iron-Silicon Bond and Implications for the Mechanism of Transition-Metal-Catalyzed Hydrosilation of Alkenes," Journal of the American Chemical Society, vol. 108, pp. 3366-3374 (1986).

Russell et al., "Synthesis of Aryl-Substituted Bis(imino)pyridine Iron Dinitrogen Complexes," Inorg. Chem. 2010, 49, 2782-2792.

Sacconi et al., "High-spin Five-Co-Ordinate Nickel (II) and Cobalt (II) Complexes with 2,6-Diacetylepyridinebis(imines)," J. Chem. Soc. (a), 1968, 1510-1515.

Seki et al., "Single-Operation Synthesis of Vinyl silanes from Alkenes and Hydrosilanes with the Aid of Ru (CO)12," Am. Chem. Soc., J. Org. Chem. 1986, 51, 3890-3895, Osaka, Japan.

Speier, John L., et al., "The Addition of Silicon Hydrides to Olefinic Double Bonds. Part II. The Use of Group VIII Metal Catalysts," Journal of the American Chemical Society, vol. 79, pp. 974-979 (1956).

Ittel et al., DuPont's Versipol®Late Metal Polymerization Catalysts, http://www.nacatsoc.org/18nam/Orals/044-Ittel-DuPont's%20Versipol%C2%AE%20Late%20Metal%20Polymerization.pdf.

Suzuki, et al., "Random and block copolymerizations of norbornene with conjugated 1,3-dienes catalyzed by novel No compounds involving N- or O-donated ligands" Reactive & Functional Polymers 59 (2004) 253-266, May 6, 2004.

Toma et al., J. Braz. Chem. Soc., vol. 7, No. 6, 391-394, 1996.

Tondreau et al., "Bis(imino)pyridine Iron Complexes for Aldehyde and Ketone Hydrosilylation," Am. Chem. Soc., 2008, vol. 10, No. 13, 2789-2792.

Tondreau, et al., "Enantiopure Pyridine Bis(oxazoline) "Pybox" and Bis(oxazoline) "Box" iron Dialkyl Complexes: Comparison to Bis(imino)pyridine Compounds and Application to Catalytic Hydrosilylation of Ketones," Organometallics, Jun. 9, 2009, 28(13), 3928-3940.

Yeung, et al., "Cobalt and iron complexes of chiral C1- and C2-terpyridines: Synthesis, characterizationa dn use in catalytic asymmetric cyclopropanation of styrenes." Inorganica Chimica Acta 362 (2009) 3267-3273.

Atienza, et al., "Olefin hydrosilylation and dehydrogenative silylation with bis(imino) pyridine iron and cobalt catalysts," Abstracts of Papers, 244th ACS National Meeting & Exposition, Philadelphia, PA, Aug. 19-23, 2012.

Atienza, "Reactivity of Bis(Iminio)Pyridine Cobalt Complexes in C—H Bond Activation and Catalytic C—C and C—Si Bond Formation" PhD thesis, Jun. 2013, Princeton University.

Shaikh et al., "Iron-Catalyzed Enantioselevtive Hydrosilylation of Keytones," Angew. Chem. Int. Ed., 2008, 47, 2497-2501.

De Bo et al., "Hydrosilylation of Alkynes Mediated by N-heterocyclic Carben Platinum(0) Complexes," Organometallics, 2006, 25, 1881-1890.

Boudjouk et al., "Exclusive 13-hydrosilylation of acrylates catalysed by copper-tetramethylethylenediamine," Journal of Organometallic Chemistry, Jan. 1, 1993, pp. 41-43.

Brookhart et al., "Mechanism of a cobalt(III)-catalyzed olefin hydrosilation reaction: direct evidence for a silyl migration pathway," J. Am. Chem. Soc. 1993, 115, 2151.

Castro, Pascel M. et al., "Iron-Based Catalysts Bearing Bis(imido)-Pyridine Ligands for the Polymerization of tert-Butyl Acrylate," Journal of Polymer Science: Part A: Polymer Chemistry, vol. 41, pp. 1380-1389 (2003).

Cornish, et al., "Homogeneous catalysis: VI. Hydrosilylation using tri(pentanedionato)rhodium(III) or tetrakis(μ-acetato) Dirhodium(II) as Catalysts," Journal of Organometallic Chemistry, Elsevier-Sequoia S.A. Lausanne, CH, vol. 172, No. 2, Jun. 12, 1979, pp. 153-163.

Chuit et al. "Reactivity of penta- and hexacoordinate silicon compounds and their role as reaction intermediates," 2, Chem. Rev. 1993, 93, 1371-1448.

De Rycke et al., "Toward reactant encapsulation for substrate-selectivity," Tetrahedron Lett. 2012, 53, 462.

Doucette, "Homogeneous Iron Catalysts With Redox-Active Ligands: Synthesis and Electronic Structure," Dissertation Cornell University, Aug. 2006.

(56) References Cited

OTHER PUBLICATIONS

Doyle et al., "Addition/Elimination in the Rhodium(II) Perfluorobutyrate Catalyzed Hydrosilylationo of 1-Alkenes. Rhodium Hydride Promoted Isomerization and Hydrogenation," Organometallics, 1992, 11, 549-555, San Antonio, Texas.

Falck, J. R. et al. "Iridium-Catalyzed (Z)-Trialkylsilylation of Terminal Olefins," J. Org. Chem. 2010, 75, 1701.

Figgins et al., "Complexes of Iron(II), Cobalt(II) and Nickel(II) with Biacetyl-bis-methlylimine, 20Pyridinal-methylimine and 2,6-Pyridindial-bis-methylimine" J. Am. Chem. Soc. 1960, vol. 82, 820-824.

Gandon, et al., "Silicon-Hydrogen Bond Activation and Hydrosilylation of Alkenes Mediated by CpCo Complexes: A Theoretical Study," J. Am. Chem. Soc. 2009, 131, 3007.

Hori et al, "Ruthenium Complex-Catalyzed Silylation of Olefins. Selective Sysnthesis of Allysilanes," Bull. Chem. Soc. Jpn., 1988, 61, 3011-3013, Kyoto, Japan.

Itoh et al, "Disproportionation reactions of organohydrosilanes in the presence of base catalysts" J. Organomet. Chem., 2001, 629, 1-6.

Ivchenko et al., "A convenient approach for the synthesis of 2,6-diformyl- and 2,6-diacetylpyridines," Tetrahedron Lett. 2013, 54, 217.

Fruchtel et al; "Organic Chemistry on Solid Supports," Angewandte Chemie International Edition in English, 1996, vol. 35, Issue 1, pp. 17-42.

Junge et al., "Iron-Catalyzed Reduction of Carboxylic Esters to Alcohols," European Journal of Organic Chemistry, vol. 2013, No. 11, Mar. 1, 2013, pp. 2016-2065.

Knijnenburg et al., "Olefin hydrogenation using diimine pyridine complexes of Co and Rh," Journal of Molecular Catalysis, 232 (2005), No. 1-2, pp. 151-159.

Marciniec, Bogdan, "Catalysis by Transition Metal Complexes of Alkene Silylation—Recent Progress and Mechanistic Implications," Coordination Chemistry Reviews, 249 (2009) 2374-2390.

Marciniec et al. "Encyclopedia of Catalysis" pp. 6, 7, and 20, Mar. 5, 2010.

Martinez, Remi et al., "C—C Bond Formation via C—H Bond Activation Using an in Situ-Generated Ruthenium Catalyst," Journal of the American Chemical Society, vol. 131, pp. 7887-7895 (2009).

McAtee et al, "Rational Design of a Second Generation Catalyst for Preparation of Allylsilanes Using the SilylHeck Reaction," J. Am. Chem. Soc. 2014, 136 (28), 10166-10172.

Bareille et al., "First Titanium-Catalyzed anti-1,4-Hydrosilylation of Dienes," Organometallics, 2005, 24(24), 5802-5806.

Nishiyama et al., "An Iron-Catalysed Hydrosilylation of Ketones," Chem. Commun., Royal Society of Chemistry, 2007, 160-762.

Furuta et al., "Highly efficient catalytic system for hydrosilylation of ketones with iron(II) acetate—thiophenecarboxylate," Tetrahedron Letters, 2008, vol. 49, Issue 1, pp. 110-113.

Ojima et al., "Regioselective hydrosilylation of 1,3-dienes catalyzed by phosphine complexes of palladium and rhodium," J. Organomet. Chem. 1978, 157, 359-372.

Pettigrew, "Synthetic Lubricants and High Performance Fluids, Ch. 12 Silahydrcarbons" (second edition), L. R. Rudnick and L R. Shubkin (Editors), Marcel Dekker, NY 1999, pp. 287-296.

Poyatos, Macarena et al., "Coordination Chemistry of a Modular N,C—Chelating Oxazole-Carbene Ligand and Its Applications in Hydrosilylation Catalysis," Organometallics, vol. 25, pp. 2634-2641 (2006).

Reiff, W. M. et al., "Mono(2,2',2"-terpyridine) Complexes of Iron(II)," Journal of Inorganic Chemistry, vol. 8, No. 9, pp. 2019-2021 (1969).

Parker et al. "1,2-Selective Hydrosilylation of Conjugated Dienes," J. Am. Chem. Soc., 2014, 136 (13), pp. 4857-4860.

Benkeser et al., "Chloroplatinic acid catalyzed additions of silanes to isoprene," J. Organomet. Chem. 1978, 156, 235-244.

Schmidt, Roland et al., "Heterogenized Iron(II) Complexes as Highly Active Ethene Polymerization Catalysts," Journal of Molecular Catalysis A: Chemical, vol. 179, pp. 155-173 (2002).

Shaikh et al., "A Convenient and General Iron-Catalyzed Hydrosilylation of Aldehydes," Organic Letters, vol. 9, No. 26, Dec. 1, 2007, pp. 5429-5432.

Small, B. L., et al. "Highly Active Iron and Cobalt Catalysts for the Polymerization of Ethylene," J. Am. Chem. Soc. 1998, 120(16), 4049-4050.

Greenhalgh et al.,"Iron-Catalysed Chemo-, Regio-, and Stereoselective Hydrosilylation of Alkenes and Alkynes using a Bench-Stable Iron(II) Pre-Catalyst," Adv. Synth. Cata. 2014, 356(2-3), 584-590.

Woo et al., "Redistribution of Bos- and Tris(silyl)methanes Catalyzed by Red-Al," Bull. Korean. Chem. Soc. 1996, 17, 123-125.

Wu et al., "A Strategy for the Synthesis of Well-Defined Iron Catalysts and Application to Regioselective Diene Hydrosilylation," Journal of the American Chemical Society, vol. 132, No. 38. Sep. 29, 2010, pp. 13214-13216.

Yi, Chae S. et al., "Regioselective Intermolecular Coupling Reaction of Arylketones and Alkenes Involving C—H Bond Activation Catalyzed by an in Situ Formed Cationic Ruthenium Hydride Complex," Organometallics, vol. 28, pp. 4266-4268 (2009).

Zhang et al., "Ferrous and Cobaltous Chlorides Bearing 2,8-Bis(imino)quinolines: Highly Active Catalysts for Ethylene Polymerization at High Temperature," Organometallics, vol. 29, pp. 1168-1173 (2010).

Zhu et al., "(Py)2Co(CH2SiMe3)2 As an Easily Accessible Source of "CoR2"," Organometallics, 2010, 29 (8), 1897-1908.

International Search Report and Written Opinion of the International Searching Authority for PCT/US2014/066348 mailed Feb. 3, 2015.

* cited by examiner

COBALT CATALYSTS AND THEIR USE FOR HYDROSILYLATION AND DEHYDROGENATIVE SILYLATION

CROSS REFERENCE TO RELATED APPLICATIONS

The present application claims priority to and the benefit of U.S. Provisional Application No. 61/906,210 entitled "Cobalt Catalysts and Their Use for Hydrosilylation and Dehydrogenative Silylation," filed on Nov. 19, 2013, the entire disclosure of which is incorporated herein by reference in its entirety.

FIELD OF THE INVENTION

This invention relates generally to transition metal-containing compounds, more specifically to cobalt complexes containing pyridine di-imine ligands and their use as catalysts for hydrosilylation and dehydrogenative silylation reactions.

BACKGROUND

Hydrosilylation chemistry, typically involving a reaction between a silyl hydride and an unsaturated organic group, is the basis for synthetic routes to produce commercial silicone-based products like silicone surfactants, silicone fluids and silanes as well as many addition cured products like sealants, adhesives, and coatings. Typical hydrosilylation reactions use precious metal catalysts to catalyze the addition of a silyl-hydride (Si—H) to an unsaturated group, such as an olefin. In these reactions, the resulting product is a silyl-substituted, saturated compound. In most of these cases, the addition of the silyl group proceeds in an anti-Markovnikov manner, i.e., to the less substituted carbon atom of the unsaturated group. Most precious metal catalyzed hydrosilylations only work well with terminally unsaturated olefins, as internal unsaturations are generally non-reactive or only poorly reactive. There are currently only limited commercially viable methods for the general hydrosilylation of olefins where after the addition of the Si—H group there still remains an unsaturation in the original substrate. This reaction, termed a dehydrogenative silylation, has potential uses in the synthesis of new silicone materials, such as silanes, silicone fluids, crosslinked silicone elastomers, and silylated or silicone-crosslinked organic polymers such as polyolefins, unsaturated polyesters, and the like.

Various precious metal complex catalysts are known in the art including a platinum complex containing unsaturated siloxanes as ligands, which is known in the art as Karstedt's catalyst. Other platinum-based hydrosilylation catalysts include Ashby's catalyst, Lamoreaux's catalyst, and Speier's catalyst.

Other metal-based catalysts have been explored including, for example, rhodium complexes, iridium complexes, palladium complexes and even first-row transition metal-based catalysts to promote limited hydrosilylations and dehydrogenative silylations.

U.S. Pat. No. 5,955,555 discloses the synthesis of certain iron or cobalt pyridine di-imine (PDI) complexes bearing two ionic ligands. The preferred anions are chloride, bromide, and tetrafluoroborate. U.S. Pat. No. 7,442,819 discloses iron and cobalt complexes of certain tricyclic ligands containing a "pyridine" ring substituted with two imino groups. U.S. Pat. Nos. 6,461,994, 6,657,026 and 7,148,304 disclose several catalyst systems containing certain transitional metal-PDI complexes. U.S. Pat. No. 7,053,020 discloses a catalyst system containing, inter alia, one or more bisarylimino pyridine iron or cobalt catalyst. Chirik et al describe bisarylimino pyridine cobalt complexes with anionic ligands (Inorg. Chem. 2010, 49, 6110 and JACS. 2010, 132, 1676.) However, the catalysts and catalyst systems disclosed in these references are described for use in the context of olefin hydrogenation, polymerizations and/or oligomerisations, not in the context of dehydrogenative silylation reactions. U.S. Pat. No. 8,236,915 discloses hydrosilylation using Mn, Fe, Co, and Ni catalysts containing pyridinediimine ligands. However, these catalysts are sensitive to air.

There is a continuing need in the silylation industry for non-precious metal-based catalysts that are effective for efficiently and selectively catalyzing hydrosilylation and/or dehydrogenative silylations. There is also a need for metal-based catalysts that are air stable. Many metal-based catalysts, including those based on iron or cobalt, are not stable under atmospheric conditions. This makes such materials generally unsuitable for application on a production or industrial scale.

Further, many industrially important homogeneous metal catalysts suffer from the drawback that following consumption of the first charge of substrates, the catalytically active metal is lost to aggregation and agglomeration and its beneficial catalytic properties are substantially diminished via colloid formation or precipitation. This is a costly loss, especially for noble metals such as Pt. Heterogeneous catalysts are used to alleviate this problem but have limited use for polymers and also have lower activity than homogeneous counterparts. For example, the two primary homogeneous catalysts for hydrosilylation, Speier's and Karstedt's, often lose activity after catalyzing a charge of olefin and silyl- or siloxy-hydride reaction. If a single charge of the homogeneous catalyst could be re-used for multiple charges of substrates, then catalyst and process cost advantages would be significant.

SUMMARY

The present invention provides cobalt complexes. The cobalt complexes can be used as catalysts for hydrosilylation and/or dehydrogenative silylation processes. Additionally, the present cobalt complexes exhibit air-stability that allows handling under atmospheric conditions.

In one aspect, the present invention provides a complex of the formula:

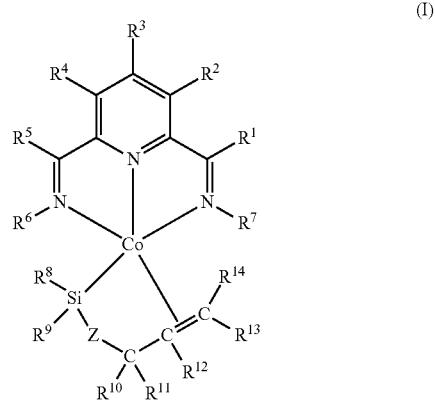

(I)

wherein each occurrence of $R^1$, $R^2$, $R^3$, $R^4$, $R^5$, $R^8$, $R^9$, $R^{10}$, $R^{11}$, $R^{12}$, $R^{13}$, and $R^{14}$ is independently hydrogen, a C1-C18 alkyl, a C1-18 substituted alkyl, a C6-C18 aryl, a substituted C6-C 18 aryl, or an inert substituent, wherein one or more of $R^1$-$R^5$ and $R^8$-$R^{14}$, other than hydrogen, optionally contain at least one heteroatom; each occurrence of $R^6$ and $R^7$ is independently a C1-C18 alkyl, a C1-C18 substituted alkyl, a C6-C18 aryl or a substituted C6-C18 aryl, wherein one or both $R^6$ and $R^7$ optionally contain at least one heteroatom; optionally any two of $R^1$, $R^2$, $R^3$, $R^4$, $R^5$, $R^6$, and $R^7$ vicinal to one another, $R^1$-$R^2$, and/or $R^4$-$R^5$ taken together may form a ring being a substituted or unsubstituted, saturated, or unsaturated cyclic structure, with the proviso that $R^5$-$R^6$ and $R^1$-$R^7$ are not taken to form a terpyridine ring; and Z is O, $NR^{15}$, or $CR^{16}R^{17}$, wherein $R^{15}$, $R^{16}$, and $R^{17}$ is independently hydrogen, a C1-18 alkyl, C1-C18 substituted alkyl, a C6-C18 aryl, or a substituted C6-C18 aryl group, an alkaryl group, an aralkyl group, and one or more of $R^{15}$, $R^{16}$, and $R^{17}$ optionally contain at least one heteroatom.

In one embodiment, Z is O, and $R^8$ and $R^9$ are independently chosen from a C1-C4 alkyl or a C6-C10 aryl. In one embodiment, Z is O, and $R^8$ and $R^9$ are independently chosen from methyl or phenyl.

In one embodiment, $R^6$ and $R^7$ are independently chosen from a C1-C8 linear, branched, or cyclic alkyl, a C6-C18 aryl, or a substituted C6-C18 aryl. In one embodiment, $R^6$ and/or $R^7$ comprise an aryl of the formula:

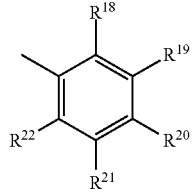

wherein each occurrence of $R^{18}$, $R^{19}$, $R^{20}$, $R^{21}$, and $R^{22}$ is independently hydrogen, a C1-C18 alkyl, a C1-C18 substituted alkyl, a C6-C18 aryl, a substituted C6-C18 aryl, or an inert substituent, wherein one or more of $R^{18}$-$R^{22}$, other than hydrogen, optionally contain at least one heteroatom.

In one embodiment, $R^{18}$, $R^{20}$, and $R^{22}$ are a C1-C4 alkyl, and $R^{19}$ and $R^{21}$ are hydrogen.

In one embodiment, the complex is of the formula:

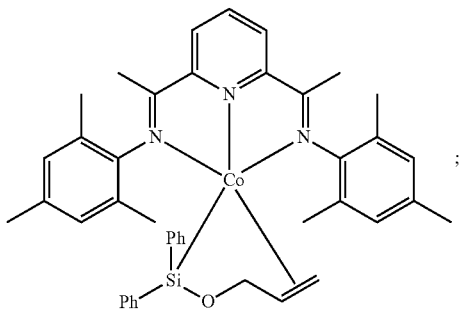

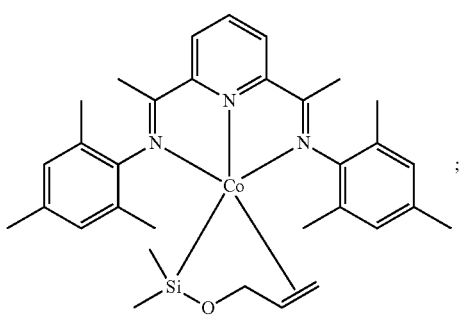

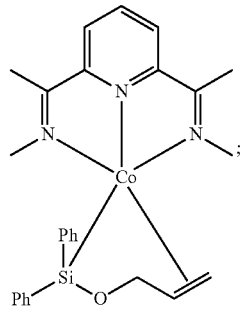

or

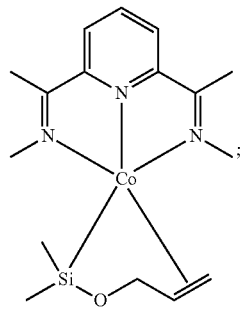

In one embodiment, the complex is immobilized on a support. In one embodiment, the support is chosen from carbon, silica, alumina, $MgCl_2$, zirconia, polyethylene, polypropylene, polystyrene, poly(aminostyrene), sulfonated polystyrene, or a combination of two or more thereof. In one embodiment, at least one of $R^1$, $R^2$, $R^3$, $R^4$, $R^5$, $R^6$, and/or $R^7$ comprises a functional group that covalently bonds with the support.

In one aspect, the present invention provides, a process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (I) or an adduct thereof:

(I)

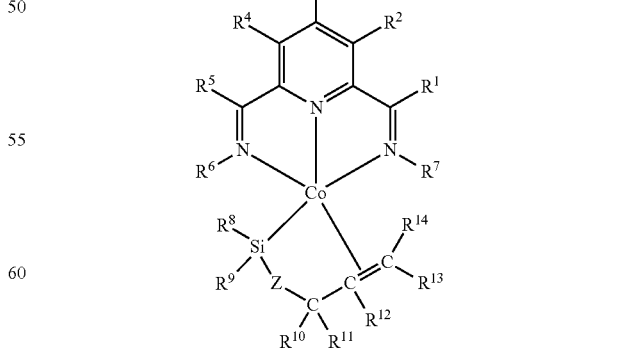

wherein each occurrence of $R^1$, $R^2$, $R^3$, $R^4$, $R^5$, $R^8$, $R^9$, $R^{10}$, $R^{11}$, $R^{12}$, $R^{13}$, and $R^{14}$ is independently hydrogen, a C1-C18 alkyl, a C1-C18 substituted alkyl, a C6-C18 aryl, a substituted C6-C18 aryl, or an inert substituent, wherein one or more of $R^1$-$R^5$ and $R^8$-$R^{14}$, other than hydrogen, optionally contain at least one heteroatom; each occurrence of $R^6$ and $R^7$ is independently a C1-C18 alkyl, a C1-C18 substituted alkyl, a C6-C18 aryl or a substituted C6-C18 aryl, wherein one or both $R^6$ and $R^7$ optionally contain at least one heteroatom; optionally any two of $R^1$, $R^2$, $R^3$, $R^4$, $R^5$, $R^6$, and $R^7$ vicinal to one another, $R^1$-$R^2$, and/or $R^4$-$R^5$ taken together may form a ring being a substituted or unsubstituted, saturated, or unsaturated cyclic structure, with the proviso that $R^5$-$R^6$ and $R^1$-$R^7$ are not taken to form a terpyridine ring; and Z is O, $NR^{15}$, or $CR^{16}R^{17}$, wherein $R^{15}$, $R^{16}$, and $R^{17}$ is independently hydrogen, a C1-C18 alkyl, C1-C18 substituted alkyl, a C6-C18 aryl, or a substituted C6-C18 aryl group, an alkaryl group, an aralkyl group, and one or more of $R^{15}$, $R^{16}$, and $R^{17}$ optionally contains at least one heteroatom.

In one embodiment, one or both of $R^6$ and $R^7$ comprise an aryl of the formula:

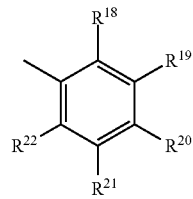

wherein each occurrence of $R^{18}$, $R^{19}$, $R^{20}$, $R^{21}$, and $R^{22}$ is independently hydrogen, a C1-C18 alkyl, a C1-C18 substituted alkyl, a C6-C18 aryl, a substituted C6-C18 aryl, or an inert substituent, wherein one or more of $R^{18}$-$R^{22}$, other than hydrogen, optionally contain at least one heteroatom.

In one embodiment, $R^{18}$ and $R^{22}$ are independently methyl, ethyl or isopropyl groups and $R^3$ is hydrogen or methyl.

In one embodiment, $R^{18}$, $R^{20}$, and $R^{22}$ are each methyl.

In one embodiment, $R^1$ and $R^5$ are independently methyl or phenyl groups.

In one embodiment, $R^2$, $R^3$, and $R^4$ are hydrogen.

In one embodiment, the catalyst is chosen from a complex of the formula:

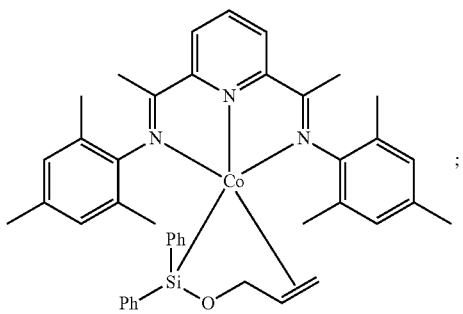

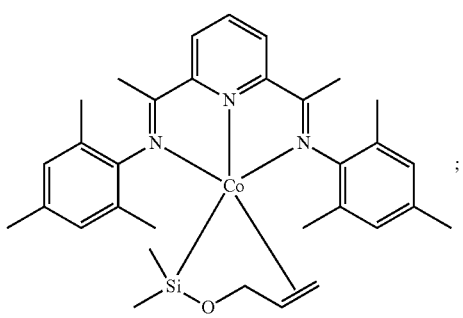

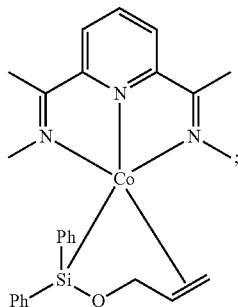

or

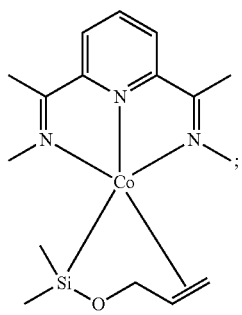

or a combination of two or more thereof.

In one embodiment, the process further comprises removing the complex and/or derivatives thereof from the dehydrogenative silylated product.

In one embodiment, the dehydrogenatively silylated product comprises a silane or siloxane containing a silyl group and an unsaturated group.

In one embodiment, the unsaturated group is in the alpha or beta position relative to the silyl group.

In one embodiment, the molar ratio of the unsaturated group in said component (a) relative to the silylhydride functional group in said component (b) is equal to 2:1 or greater.

In one embodiment, the dehydrogenatively silylated product contains two or more terminal silyl groups derived from component (b).

In one embodiment, component (a) is a mono-unsaturated compound. In one embodiment, component (a) is selected from the group consisting of an alkyne or an olefin; a cycloalkene; an alkyl-capped allyl polyether; a vinyl-functional alkyl-capped allyl or methallyl polyether; an alkyl-capped terminally unsaturated amine; an alkyne; terminally unsaturated acrylate or methacrylate; unsaturated aryl ether; vinyl-functionalized polymer or oligomer; vinyl-functionalized and/or terminally unsaturated alkenyl-functionalized silane and/or silicone; an unsaturated fatty acid; an unsaturated ester; or a combination of two or more thereof.

In one embodiment, the reaction is conducted in the presence of a solvent selected from the group consisting of hydrocarbons, halogenated hydrocarbons, ethers, and combinations thereof.

In one embodiment, the reaction is carried out at a temperature of −40° C. to 200° C.

In one embodiment, the silylated product comprises an anti-Markovnikov addition product, a Markovnkiov addition product, or a combination thereof.

In one aspect, the present invention provides a process for producing a crosslinked material, comprising reacting a mixture comprising (a) a silyl-hydride containing polymer, (b) a mono-unsaturated olefin or an unsaturated polyolefin, or combinations thereof and (c) a catalyst, optionally in the presence of a solvent, in order to produce the crosslinked material, wherein the catalyst is a complex of the Formula (I) or an adduct thereof;

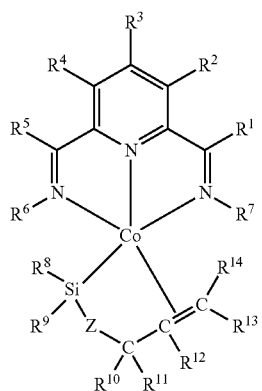
(I)

wherein each occurrence of $R^1$, $R^2$, $R^3$, $R^4$, $R^5$, $R^8$, $R^9$, $R^{10}$, $R^{11}$, $R^{12}$, $R^{13}$, and $R^{14}$ is independently hydrogen, a C1-C18 alkyl, a C1-C18 substituted alkyl, a C6-C18 aryl, a substituted C6-C18 aryl, or an inert substituent, wherein one or more of $R^1$-$R^5$, and $R^8$-$R^{14}$ other than hydrogen, optionally contain at least one heteroatom; each occurrence of $R^6$ and $R^7$ is independently a C1-C18 alkyl, a C1-C18 substituted alkyl, a C6-C18 aryl or a substituted C6-C18 aryl, wherein one or both $R^6$ and $R^7$ optionally contain at least one heteroatom; optionally any two of $R^1$, $R^2$, $R^3$, $R^4$, $R^5$, $R^6$, and $R^7$ vicinal to one another, $R^1$-$R^2$, and/or $R^4$-$R^5$ taken together may form a ring being a substituted or unsubstituted, saturated, or unsaturated cyclic structure, with the proviso that $R^5$-$R^6$ and $R^1$-$R^7$ are not taken to form a terpyridine ring; and Z is O, $NR^{15}$, or $CR^{16}R^{17}$, wherein $R^{15}$, $R^{16}$, and $R^{17}$ is independently hydrogen, a C1-C18 alkyl, C1-C18 substituted alkyl, a C6-C18 aryl, or a substituted C6-C18 aryl group, an alkaryl group, an aralkyl group, and one or more of $R^{15}$, $R^{16}$, and $R^{17}$ optionally contains at least one heteroatom.

In one aspect, the present invention provides a process for the hydrosilylation of a composition comprising hydrosilylation reactants chosen from (a) an unsaturated compound containing at least one unsaturated functional group, and (b) a silyl hydride containing at least one silylhydride functional group, the process comprising contacting the composition comprising the hydrosilylation reactants with a complex of the formula:

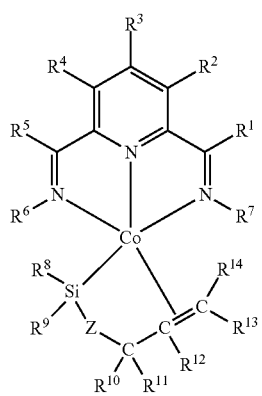
(I)

wherein each occurrence of $R^1$, $R^2$, $R^3$, $R^4$, $R^5$, $R^8$, $R^9$, $R^{10}$, $R^{11}$, $R^{12}$, $R^{13}$, and $R^{14}$ is independently hydrogen, a C1-C18 alkyl, a C1-C18 substituted alkyl, a C6-C18 aryl, a substituted C6-C18 aryl, or an inert substituent, wherein one or more of $R^1$-$R^5$, and $R^8$-$R^{14}$ other than hydrogen, optionally contain at least one heteroatom; each occurrence of $R^6$ and $R^7$ is independently a C1-C18 alkyl, a C1-C18 substituted alkyl, a C6-C18 aryl or a substituted C6-C18 aryl, wherein one or both of $R^6$ and $R^7$ optionally contain at least one heteroatom; optionally any two of $R^1$, $R^2$, $R^3$, $R^4$, $R^5$, $R^6$, and $R^7$ vicinal to one another, $R^1$-$R^2$, and/or $R^4$-$R^5$ taken together may form a ring being a substituted or unsubstituted, saturated, or unsaturated cyclic structure with the proviso that $R^5$-$R^6$ and $R^1$-$R^7$ are not taken to form a terpyridine ring; and Z is O, $NR^{15}$, or $CR^{16}R^{17}$, wherein $R^{15}$, $R^{16}$, and $R^{17}$ is independently hydrogen, a C1-C18 alkyl, C1-C18 substituted alkyl, a C6-C18 aryl, or a substituted C6-C18 aryl group, an alkaryl group, an aralkyl group, and one or more of $R^{15}$, $R^{16}$, and $R^{17}$ optionally contains at least one heteroatom.

In one embodiment, Z is O, and $R^8$ and $R^9$ are independently chosen from a C1-C8 alkyl and C6-C18 aryl. In one embodiment, Z is O, and $R^8$ and $R^9$ are independently chosen from methyl or phenyl.

In one embodiment, $R^6$ and $R^7$ are independently chosen from a C1-C8 linear, branched, or cyclic alkyl, a C6-C18 aryl, or a substituted C6-C18 aryl. In one embodiment, wherein $R^6$ and $R^7$ are each methyl.

In one embodiment, $R^2$, $R^3$, and $R^4$ are each hydrogen.

In one embodiment, wherein $R^1$ and $R^5$ are each methyl.

In one embodiment, the complex is of the formula:

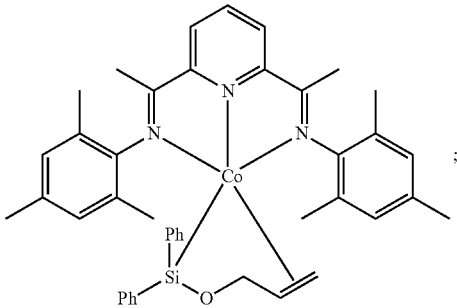

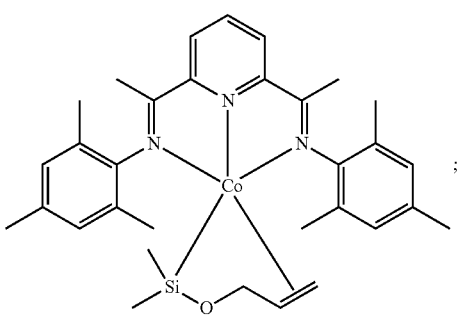

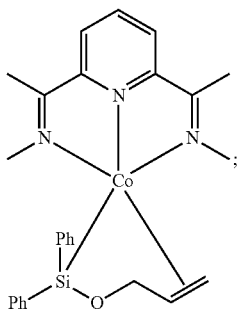

or

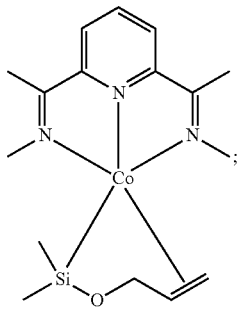

or a combination thereof.

In one embodiment, the silyl hydride is chosen from one or a combination of compounds of the formulas:

$$R^{23}{}_m SiH_p X_{4-(m+p)};$$

$$M_a M^H{}_b D_c D^H{}_d T_e T^H{}_f Q_g;$$

$$R^{29}{}_3 Si(CH_2 R^{29})_x SiOSiR^{29}{}_2 (OSiR^{29}{}_2)_y OSiR^{29}{}_2 H;$$

$$R^{29}{}_3 Si(CHR^{29})_x SiR^{29}{}_2 H,$$

or a combination of two or more thereof, where each $R^{23}$ is independently a substituted or unsubstituted aliphatic or aromatic hydrocarbyl group; X is halogen, alkoxy, acyloxy, or silazane; m is 0-3; p is 1-3 with the proviso that the silicon remains tetravalent; M represents a monofunctional group of formula $R^{24}{}_3 SiO_{1/2}$; a D represents a difunctional group of formula $R^{24}{}_2 SiO_{2/2}$; a T represents a trifunctional group of formula $R^{24} SiO_{3/2}$; Q represents a tetrafunctional group of formula $SiO_{4/2}$; $M^H$ represents $HR^{24}{}_2 SiO_{1/2}$, $T^H$ represents $HSiO_{3/2}$, and $D^H$ group represents $R^{24} HSiO_{2/2}$; each occurrence of $R^{24}$ is independently a $C_1$-$C_{18}$ alkyl, a $C_1$-$C_{18}$ substituted alkyl, a $C_6$-$C_{14}$ aryl or substituted aryl, wherein $R^{24}$ optionally contains at least one heteroatom; subscripts a, b, c, d, e, f, and g are such that the molar mass of the compound is between 100 and 100,000 Dalton; each occurrence of $R^{29}$ is independently C1-C18 alkyl, C1-C18 substituted alkyl, C6-C14 aryl or substituted aryl; x is 1-8, and y is 0-10.

In one embodiment, the unsaturated compound (a) is chosen from an unsaturated polyether; a vinyl functionalized alkyl capped allyl or methylallyl polyether; a terminally unsaturated amine; an alkyne; a C2-C45 olefins; an unsaturated epoxide; a terminally unsaturated acrylate or methyl acrylate; an unsaturated aryl ether; an unsaturated aromatic hydrocarbon; unsaturated cycloalkane; a vinyl-functionalized polymer or oligomer; a vinyl-functionalized silane, a vinyl-functionalized silicone, terminally unsaturated alkenyl-functionalized silane and/or silicone or a combination of two or more thereof.

In one embodiment, the unsaturated compound (a) is chosen from one or more polyethers having the general formula:

$$R^{25}(OCH_2CH_2)_z(OCH_2CHR^{27})_w—OR^{26};$$

and/or $$R^{26}O(CHR^{27}CH_2O)_w(CH_2CH_2O)_z—CR^{28}{}_2—C\equiv C—CR^{28}{}_2(OCH_2CH_2)_z(OCH_2CHR^{27})_w R^{26}$$

wherein $R^{25}$ is chosen from an unsaturated organic group having from 2 to 10 carbon atoms; $R^{26}$ is independently chosen from a hydrogen, vinyl,, allyl, methallyl, or a polyether capping group of from 1 to 8 carbon atoms, an acyl group, a beta-ketoester group, or a trialkylsilyl group; $R^{27}$ and $R^{28}$ are independently chosen from hydrogen, a monovalent hydrocarbon group, an aryl group, an alkaryl group, and a cycloalkyl group; a Me or H are preferred for $R^{27}$; each occurrence of z is 0 to 100 inclusive; and each occurrence of w is 0 to 100 inclusive.

In one embodiment, the process further comprises removal of the catalyst composition. In one embodiment, removal of the catalyst composition is achieved by filtration.

In one embodiment, the reaction is conducted at a temperature of from about −10° C. to about 200° C.

In one embodiment, the reaction is conducted in a subatmospheric pressure.

In one embodiment, the reaction is conducted in a supra-atmospheric pressure.

In one embodiment, the present invention provides a composition produced from the various process. In one embodiment, the composition contains the catalyst or derivatives thereof. In one embodiment, the composition comprises at least one component chosen from a silane, a silicone fluid, a crosslinked silicone, or a combination of two or more thereof.

In another aspect, the present invention provides a process for producing a silylated product in the presence of the catalyst of Formula (I). In one embodiment, the process is a process for producing a hydrosilylated product. In another embodiment, the process is a process for producing a dehydrogenatively silylated product.

In one aspect, the present invention provides a process for the hydrosilylation of a composition, the process comprising contacting the composition comprising the hydrosilylation reactants with a complex of the Formula (I). In one embodiment, the hydrosilylation reactants comprise (a) an unsaturated compound containing at least one unsaturated functional group, (b) a silyl hydride containing at least one silylhydride functional group, and (c) a catalyst of Formula I or an adduct thereof, optionally in the presence of a solvent.

In one aspect, the present invention provides a process for producing a dehydrogenatively silylated product, the process comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (I) or an adduct thereof.

DETAILED DESCRIPTION

The invention relates to cobalt complexes containing pyridine di-imine ligands and their use as efficient hydrosilylation catalysts and/or dehydrogenative silylation and catalysts. In one embodiment of the invention, there is provided a complex of the Formula (I), as illustrated above, wherein Co can be in any valence or oxidation state (e.g., +1, +2, or +3) for use in a hydrosilylation reaction, a dehydrogenative silylation reaction, and/or crosslinking reactions. In particular, according to one embodiment of the invention, a class of cobalt pyridine di-imine complexes has been found that are capable of hydrosilylation and/or dehydrogenative silylation reactions. The invention also addresses the advantage of reusing a single charge of catalyst for multiple batches of product, resulting in process efficiencies and lower costs.

As used herein, the term "alkyl" includes straight, branched and cyclic alkyl groups. Specific and non-limiting examples of alkyls include, but are not limited to, methyl, ethyl, propyl, isobutyl and cyclohexyl.

As used herein, the term "substituted alkyl" includes an alkyl group that contains one or more substituent groups that are inert under the process conditions to which the compound containing these groups is subjected. The substituent groups also do not substantially or deleteriously interfere with the process.

As used herein, the term "aryl" refers to a non-limiting group of any aromatic hydrocarbon from which one hydrogen atom has been removed. An aryl may have one or more aromatic rings, which may be fused, connected by single bonds or other groups. Examples of suitable aryls include, but are not limited to, tolyl, xylyl, phenyl and naphthalenyl.

As used herein, the term "substituted aryl" refers to an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the attachment can be through a heteroatom (such as nitrogen) of the heteroaromatic ring instead of a carbon. In one embodiment, the substituted aryl groups herein contain 1 to about 30 carbon atoms.

As used herein, the term "alkenyl" refers to any straight, branched, or cyclic alkenyl group containing one or more carbon-carbon double bonds, where the point of substitution can be either a carbon-carbon double bond or elsewhere in the group. Examples of suitable alkenyls include, but are not limited to, vinyl, propenyl, allyl, methallyl, ethylidenyl norbornyl, etc.

As used herein, the term "alkynyl" refers to any straight, branched, or cyclic alkynyl group containing one or more carbon-carbon triple bonds, where the point of substitution can be either at a carbon-carbon triple bond or elsewhere in the group.

As used herein, the term "unsaturated" refers to one or more double or triple bonds. In one embodiment, it refers to carbon-carbon double or triple bonds.

As used herein, the term "inert substituent" refers to a group other than hydrocarbyl or substituted hydrocarbyl, which is inert under the process conditions to which the compound containing the group is subjected. The inert substituents also do not substantially or deleteriously interfere with any process described herein that the compound in which they are present may take part in. Examples of inert substituents include, but are not limited to, halo (fluoro, chloro, bromo, and iodo), and ether such as —$OR^{30}$ wherein $R^{30}$ is hydrocarbyl or substituted hydrocarbyl.

As used herein, the term "hetero atoms" refers to any of the Group 13-17 elements except carbon, and can include, for example, oxygen, nitrogen, silicon, sulfur, phosphorus, fluorine, chlorine, bromine, and iodine.

As used herein, the term "olefin" refers to any aliphatic or aromatic hydrocarbon also containing one or more aliphatic carbon-carbon unsaturations. Such olefins may be linear, branched, or cyclic and may be substituted with heteroatoms as described above, with the proviso that the substituents do not interfere substantially or deleteriously with the course of the desired reaction to produce the dehydrogenatively silylated product.

Cobalt Complexes

The present invention provides, in one aspect, a cobalt complex, which complex can be used as a catalyst in hydrosilylation or dehydrogenative silylation reactions. The catalyst composition comprises a cobalt complex containing a pyridine di-imine (PDI) ligand and a chelating alkenyl-substituted silyl ligand with the alkenyl substitution preferred at the beta-position relative to silicon. In one embodiment, the catalyst is a complex of the Formula (I) or an adduct thereof:

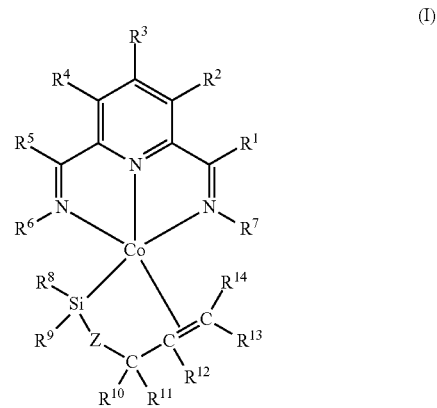

(I)

wherein each occurrence of $R^1$, $R^2$, $R^3$, $R^4$, $R^5$, $R^8$, $R^9$, $R^{10}$, $R^{11}$, $R^{12}$, $R^{13}$, and $R^{14}$ is independently hydrogen, a C1-C18 alkyl, a C1-C18 substituted alkyl, a C6-C18 aryl or substituted aryl, or an inert substituent, wherein one or more of $R^1$-$R^5$ and $R^8$-$R^{14}$ contain at least one heteroatom; each occurrence of $R^6$-$R^7$ is independently a C1-C18 alkyl, a C1-C18 substituted alkyl, a C6-C18 aryl or substituted aryl, wherein one or both of $R^6$ and $R^7$ optionally contain at least one heteroatom; optionally any two of $R^1$, $R^2$, $R^3$, $R^4$, $R^5$, $R^6$, and $R^7$ vicinal to one another, $R^1$-$R^2$, and/or $R^4$-$R^5$ taken together may form a ring being a substituted or unsubstituted, saturated, or unsaturated cyclic structure, with the proviso that $R^5$-$R^6$ and $R^1$-$R^7$ are not taken to form a terpyridine ring; and Z is O, $NR^{15}$, or $CR^{16}R^{17}$, wherein $R^{15}$, $R^{16}$, and $R^{17}$ is independently hydrogen, a C1-C18 alkyl, C1-C18 substituted alkyl, a C6-C18 aryl or substituted aryl group, an alkaryl group, an aralkyl group, and one or more of $R^{15}$, $R^{16}$, and $R^{17}$ optionally contains at least one heteroatom. In the catalyst complex Co can be in any valence or oxidation state (e.g., +1, +2, or +3).

In one embodiment, at least one of $R^6$ and $R^7$ is

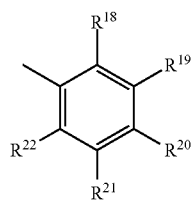

wherein each occurrence of $R^{18}$, R19, $R^{20}$, $R^{21}$, and $R^{22}$ is independently hydrogen, a C1-C18 alkyl, a C1-C18 substituted alkyl, a C6-C18 aryl or substituted aryl, or an inert substituent, wherein one or more of $R^{18}$-$R^{22}$, other than hydrogen, optionally contain at least one heteroatom. In one embodiment, $R^{18}$ and $R^{22}$ may independently include methyl, ethyl, or isopropyl groups, and $R^{20}$ may be hydrogen or methyl. In one embodiment, $R^{18}$, $R^{20}$, and $R^{22}$ are each methyl and $R^{19}$ and $R^{21}$ are hydrogen.

In one embodiment, the cobalt complex is such that $R^6$ and $R^7$ are a methyl or phenyl group, $R^1$ and $R^5$ may independently be methyl or phenyl groups; and $R^2$, $R^3$ and $R^4$ may be hydrogen.

In one embodiment, $R^8$ and $R^9$ are independently chosen from a C1-C10 alkyl, or an aryl, Z is O, and $R^{10}$-$R^{14}$ are hydrogen. In one embodiment, $R^8$ and $R^9$ are each methyl. In still another embodiment, $R^8$ and $R^9$ are each phenyl.

In one embodiment, the cobalt complex is a complex of the formula:

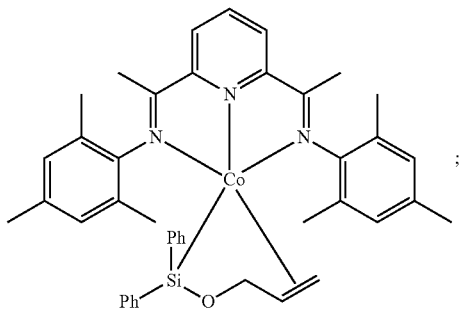

(II)

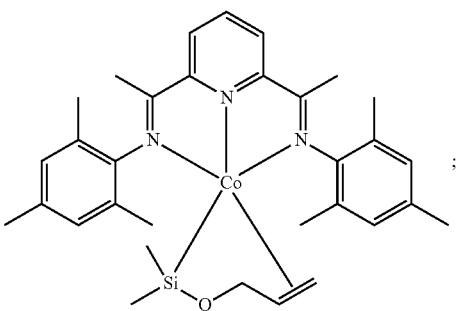

(III)

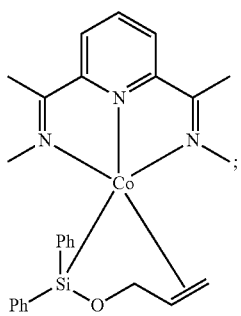

(IV)

or

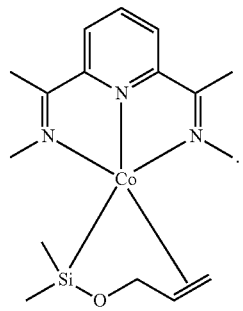

(V)

In one embodiment, the catalyst is generated by reacting a catalyst precursor prepared according to published procedure with the desired alkenyl-modified silane containing an SiH group in a solvent.

The present catalysts exhibit air stability that allows handling in the open atmosphere. Many iron or cobalt complexes previously known to catalyze hydrosilylation or dehydrogenative silylation exhibit poor air stability which limits their industrial application. The present PDI-Co complexes with the chelating alkene-modified silyl ligand, however, have been found to overcome this major drawback.

In the reaction processes of the invention, the catalysts can be unsupported or immobilized on a support material, for example, carbon, silica, alumina, $MgCl_2$ or zirconia, or on a polymer or prepolymer, for example polyethylene, polypropylene, polystyrene, poly(aminostyrene), or sulfonated polystyrene. The metal complexes can also be supported on dendrimers.

In some embodiments, for the purposes of attaching the metal complexes of the invention to a support, it is desirable that at least one of $R^1$ to $R^7$ of the metal complexes has a functional group that is effective to covalently bond to the support. Exemplary functional groups include, but are not limited to, vinyl, SH, COOH, $NH_2$ or OH groups.

Catalyzed Reactions

In accordance with the present invention, the cobalt complexes of Formula (I) can be used as a catalyst for a dehydrogenative silylation process, hydrosilylation reaction process, and/or a cross-linking reaction process. The dehydrogenative silylation and hydrosilylation processes generally comprise reacting a silyl hydride compound with an unsaturated compound having at least one unsaturated functional group.

The silyl hydride employed in the reactions is not particularly limited. It can be, for example, any compound chosen from hydrosilanes or hydrosiloxanes including those compounds of the formulas $R^{23}{}_mSiH_pX_{4-(m+p)}$ or $M_aM^H{}_bD_cD^H{}_dT_eT^H{}_fQ_g$, where each $R^{23}$ is independently a substituted or unsubstituted aliphatic or aromatic hydrocarbyl group, X is alkoxy, acyloxy, or silazane, m is 0-3, p is 1-3 (with the proviso that silicon remains tetravalent), and M, D, T, and Q have their usual meaning in siloxane nomenclature. The subscripts a, b, c, d, e, f, and g are such that the molar mass of the siloxane-type reactant is between 100 and 100,000 Dalton. In one embodiment, an "M" group represents a monofunctional group of formula $R^{24}{}_3SiO_{1/2}$, a "D" group represents a difunctional group of formula $R^{24}{}_2SiO_{2/2}$, a "T" group represents a trifunctional group of formula $R^{24}SiO_{3/2}$, and a "Q" group represents a tetrafunctional group of formula $SiO_{4/2}$, an "$M^H$" group represents $HR^{24}{}_2SiO_{1/2}$, a "$T^H$" represents $HSiO_{3/2}$, and a "$D^H$" group represents $R^{24}HSiO_{2/2}$. Each occurrence of $R^{24}$ is independently C1-C18 alkyl, C1-C18 substituted alkyl, C6-C14 aryl or substituted aryl, wherein $R^{24}$ optionally contains at least one heteroatom.

The instant invention also provides hydrosilylation with hydridosiloxanes comprising carbosiloxane linkages (for example, Si—CH$_2$—Si—O—SiH, Si—CH$_2$—CH$_2$—Si—O—SiH or Si-arylene-Si—O—SiH). Carbosiloxanes contain both the —Si-(hydrocarbylene)—Si— and —Si—O—Si— functionalities, where hydrocarbylene represents a substituted or unsubstituted, divalent alkylene, cycloalkylene or arylene group. The synthesis of carbosiloxanes is disclosed in U.S. Pat. No. 7,259,220; U.S. Pat. No. 7,326,761 and U.S. Pat. No. 7,507,775 all of which are incorporated herein in their entirety by reference. An exemplary formula for hydridosiloxanes with carbosiloxane linkages is $R^{29}_3$Si(CH$_2$R$^{29}$)$_x$SiOSiR$^{29}_2$(OSiR$^{29}_2$)$_y$OSiR$^{29}_2$H, wherein each occurrence of $R^{29}$ is independently a monovalent alkyl, cycloalkyl or aryl group such as C1-C18 alkyl, C1-C18 substituted alkyl, C6-C14 aryl or substituted aryl. No limiting examples of suitable groups include, for example, methyl, ethyl, cyclohexyl or phenyl. Additionally, $R^{29}$ independently may also be H. The subscript x has a value of 1-8, y has a value from zero to 10 and is preferably zero to 4. A specific example of a hydridocarbosiloxane is (CH$_3$)$_3$SiCH$_2$CH$_2$Si(CH$_3$)$_2$OSi(CH$_3$)$_2$H.

Hydridocarbosilanes are another class useful for the hydrosilylation and dehydrogenative silylation reactions of the instant invention. Hydridocarbosilanes have SiH bonds as well as linkages such as —Si—(CH$_2$)$_x$—Si— (wherein x is an integer greater than or equal to 1, and is preferably 1-8) and other Si-hydrocarbylene groups in the molecular formula, but no siloxane linkages. As defined above, hydrocarbylene refers to a substituted or unsubstituted divalent alkylene, cycloalkylene or arylene group. They can be linear, cyclic or branched and contain more than one SiH bond per molecule. The SiH bonds can be terminal or distributed internally along the Si-hydrocarbylene chains in the molecule. An exemplary formula for hydridocarbosilanes is $R^{29}_3$Si(CHR$^{29}$)$_x$SiR$^{29}_2$H, $R^{29}$ and x having the meanings defined above. Specific examples of hydridocarbosilanes are (CH$_3$)$_3$SiCH$_2$CH$_2$Si(CH$_3$)$_2$H, H(CH$_3$)$_2$SiCH$_2$CH$_2$Si(CH$_3$)$_2$H, (CH$_3$)$_3$SiC$_6$H$_4$Si(CH$_3$)$_2$H, (CH$_3$)$_3$SiC$_6$H$_{10}$Si(CH$_3$)$_2$H, wherein —C$_6$H$_4$— is the phenylene linkage and —C$_6$H$_{10}$— is the cyclohexylene linkage.

A variety of reactors can be used in the process of this invention. Selection is determined by factors such as the volatility of the reagents and products. Continuously stirred batch reactors are conveniently used when the reagents are liquid at ambient and reaction temperature. These reactors can also be operated with a continuous input of reagents and continuous withdrawal of dehydrogenatively silylated or hydrosilylated reaction product. With gaseous or volatile olefins and silanes, fluidized-bed reactors, fixed-bed reactors and autoclave reactors can be more appropriate.

The unsaturated compound containing at least one unsaturated functional group employed in the hydrosilylation reaction is generally not limited and can be chosen from an unsaturated compound as desired for a particular purpose or intended application. The unsaturated compound can be a mono-unsaturated compound or it can comprise two or more unsaturated functional groups. In one embodiment, the unsaturated group can be an alphatically unsaturated functional group. Examples of suitable compounds containing an unsaturated group include, but are not limited to, unsaturated polyethers such as alkyl-capped allyl polyethers, vinyl functionalized alkyl capped allyl or methylallyl polyethers; terminally unsaturated amines; alkynes; C2-C45 olefins, in one embodiment alpha olefins; unsaturated epoxides such as allyl glycidyl ether and vinyl cyclohexene-oxide; terminally unsaturated acrylates or methyl acrylates; unsaturated aryl ethers; unsaturated aromatic hydrocarbons; unsaturated cycloalkanes such as trivinyl cyclohexane; vinyl-functionalized polymer or oligomer; vinyl-functionalized and/or terminally unsaturated allyl-functionalized silane and/or vinyl-functionalized silicones; unsaturated fatty acids; unsaturated fatty esters; or combinations of two or more thereof Illustrative examples of such unsaturated substrates include, but are not limited to, ethylene, propylene, isobutylene, 1-hexene, 1-octene, 1-octadecene, styrene, alpha-methylstyrene, cyclopentene, norbornene, 1,5-hexadiene, norbornadiene, vinylcyclohexene, allyl alcohol, allyl-terminated polyethyleneglycol, allylacrylate, allyl methacrylate, allyl glycidyl ether, allyl-terminated isocyanate-or acrylate prepolymers, polybutadiene, allylamine, methallyl amine, acetylene, phenylacetylene, vinyl-pendent or vinyl-terminal polysiloxanes, vinylcyclosiloxanes, vinylsiloxane resins, other terminally-unsaturated alkenyl silanes or siloxanes, vinyl-functional synthetic or natural minerals, etc.

Unsaturated polyethers suitable for the hydrosilylation reaction include polyoxyalkylenes having the general formula:

$$R^{25}(OCH_2CH_2)_z(OCH_2CHR^{27})_w\text{—}OR^{26}; \text{and/or}$$

$$R^{26}O(CHR^{27}CH_2O)_w(CH_2CH_2O)_z\text{—}CR^{28}_2\text{—}C\!\equiv\!C\text{—}CR^{28}_2(OCH_2CH_2)_z(OCH_2CHR^{27})_wR^{26}$$

wherein $R^{25}$ denotes an unsaturated organic group containing from 2 to 10 carbon atoms such as allyl, methylallyl, propargyl or 3-pentynyl. When the unsaturation is olefinic, it is desirably terminal to facilitate smooth hydrosilylation. However, when the unsaturation is a triple bond, it may be internal. $R^{26}$ is independently hydrogen, vinyl, allyl, methallyl, or a polyether capping group of from 1 to 8 carbon atoms such as the alkyl groups: CH$_3$, n-C$_4$H$_9$, t-C$_4$H$_9$ or i-C$_8$H$_{17}$, the acyl groups such as CH$_3$COO, t-C$_4$H$_9$COO, the beta-ketoester group such as CH$_3$C(O)CH$_2$C(O)O, or a trialkylsilyl group. $R^{27}$ and $R^{28}$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. $R^{28}$ may also be hydrogen. Methyl is particularly suitable for the $R^{27}$ and $R^{28}$ groups. Each occurrence of z is 0 to 100 inclusive and each occurrence of w is 0 to 100 inclusive. In one embodiment, the values of z and w are 1 to 50 inclusive.

As indicated above, the present invention is directed, in one embodiment, to a process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (I) or an adduct thereof. In one embodiment, the process includes contacting the composition with a metal complex of the catalyst, either supported or unsupported, to cause the silyl hydride to react with the compound having at least one unsaturated group to produce a dehydrogenative silylation product, which may contain the metal complex catalyst. The dehydrogenative silylation reaction can be conducted optionally in the presence of a solvent. If desired, when the dehydrogenative silylation reaction is completed, the metal complex can be removed from the reaction product by magnetic separation and/or filtration. These reactions may be performed neat, or diluted in an appropriate solvent. Typical solvents include benzene, toluene, diethyl ether, etc. It is preferred that the reaction is performed under an inert atmosphere.

Effective catalyst usage for dehydrogenative silylation ranges from 0.001 mole percent to 5 mole percent based on the molar quantity of the alkene to be reacted. Preferred levels are from 0.005 to 1 mole percent. Reaction may be run at temperatures from about −10° C. up to 300° C., depending on the thermal stability of the alkene, silyl hydride and the specific pyridine di-imine complex. Temperatures in the range, 10-100° C., have been found to be effective for most reactions. Heating of reaction mixtures can be done using conventional methods as well as with microwave devices.

The dehydrogenative silylation reactions of this invention can be run at subatmospheric and supra-atmospheric pressures. Typically, pressures from about 1 atmosphere (0.1 MPa) to about 200 atmospheres (20 MPa), preferably to about 50 atmospheres (5.0 MPa), are suitable. Higher pressures are effective with volatile and/or less reactive alkenes which require confinement to enable high conversions.

The catalysts of the invention are useful for catalyzing dehydrogenative silylation reactions. For example, when an appropriate silyl hydride, such as triethoxy silane, triethyl silane, $MD^HM$, or a silyl-hydride functional polysiloxane (SL 6020 D1 from Momentive Performance Materials, Inc., for example) are reacted with a mono-unsaturated hydrocarbon, such as octene, dodecene, butene, etc, in the presence of the Co catalyst, the resulting product is a terminally-silyl-substituted alkene, where the unsaturation is in a beta position relative to the silyl group. A by-product of this reaction is the hydrogenated olefin. When the reaction is performed with a molar ratio of silane to olefin of 0.5:1 (a 2:1 molar ratio of olefin to silane) the resulting products are formed in a 1:1 ratio.

The reactions are typically facile at ambient temperatures and pressures, but can also be run at lower or higher temperatures (−10 to 300° C.) or pressures (ambient to 205 atmospheres, (0.1-20.5 MPa)). A range of unsaturated compounds can be used in this reaction, such as N,N-dimethylallyl amine, allyloxy-substituted polyethers, cyclohexene, and linear alpha olefins (i.e., 1-butene, 1-octene, 1-dodecene, etc.). When an alkene containing internal double bonds is used, the catalyst is capable of first isomerizing the olefin, with the resulting reaction product being the same as when the terminally-unsaturated alkene is used.

Because the double bond of an alkene is preserved during the dehydrogenative silylation reaction employing these cobalt catalysts, a singly-unsaturated olefin may be used to crosslink silyl-hydride containing polymers. For example, a silyl-hydride polysiloxane, such as SL6020 D1 $(MD_{15}D^H{}_{30}M)$, may be reacted with 1-octene in the presence of the cobalt catalysts of this invention to produce a crosslinked, elastomeric material. A variety of new materials can be produced by this method by varying the hydride polymer and length of the olefin used for the crosslinking. Accordingly, the catalysts used in the process of the invention have utility in the preparation of useful silicone products, including, but not limited to, coatings, for example release coatings, room temperature vulcanizates, sealants, adhesives, products for agricultural and personal care applications, and silicone surfactants for stabilizing polyurethane foams.

Furthermore, the dehydrogenative silylation may be carried out on any of a number of unsaturated polyolefins, such as polybutadiene, polyisoprene or EPDM-type copolymers, to either functionalize these commercially important polymers with silyl groups or crosslink them via the use of hydrosiloxanes containing multiple SiH groups at lower temperatures than conventionally used. This offers the potential to extend the application of these already valuable materials in newer commercially useful areas.

In one embodiment, dehydrogenative silylation is conducted by utilizing a cobalt catalyst of the formula (I) where $R^6$ and/or $R^7$ comprises an aryl group or a substituted aryl. In one embodiment, $R^6$ and/or $R^7$ is

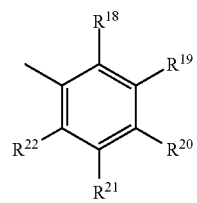

wherein each occurrence of $R^{18}$, $R^{19}$, $R^{20}$, $R^{21}$, and $R^{22}$ is independently hydrogen, a C1-C18 alkyl, a C1-C18 substituted alkyl, an aryl, a substituted aryl, or an inert substituent, wherein one or more of $R^{18}$-$R^{22}$, other than hydrogen, optionally contain at least one heteroatom. In one embodiment, $R^{18}$ and $R^{22}$ may independently include methyl, ethyl, or isopropyl groups, and $R^{20}$ may be hydrogen or methyl. In one embodiment, $R^{18}$, $R^{20}$, and $R^{22}$ are each methyl and $R^{19}$ and $R^{21}$ are hydrogen. In one embodiment, the cobalt complex employed in the dehydrogenative silylation process is a complex of Formula (II), Formula (III) or a combination thereof.

The catalyst complexes of the invention are efficient and selective in catalyzing dehydrogenative silylation reactions. For example, when the catalyst complexes of the invention are employed in the dehydrogenative silylation of an alkyl-capped allyl polyether or a compound containing an unsaturated group, the reaction products are essentially free of unreacted alkyl-capped allyl polyether and its isomerization products or unreacted compound with the unsaturated group. Further, when the compound containing an unsaturated group is an unsaturated amine compound, the dehydrogenatively silylated product is essentially free of internal addition products and isomerization products of the unsaturated compound. In one embodiment, where the unsaturated starting material is an olefin, the reaction is highly selective for the dehydrogenative silylated product, and the reaction products are essentially free of any alkene by-products. As used herein, "essentially free" is meant no more than 10 wt. %, preferably 5 wt. % based on the total weight of the dehydrogenative silylation product. "Essentially free of internal addition products" is meant that silicon is added to the terminal carbon.

The cobalt complexes can also be used as a catalyst for the hydrosilylation of a composition containing a silyl hydride and a compound having at least one unsaturated group. The hydrosilylation process includes contacting the composition with a cobalt complex of the Formula (I), either supported or unsupported, to cause the silyl hydride to react with the compound having at least one aliphatically unsaturated group to produce a hydrosilylation product. The hydrosilylation product may contain the components from the catalyst composition. The hydrosilylation reaction can be conducted optionally in the presence of a solvent, at subatmospheric or supra-atmospheric pressures and in batch or continuous processes. The hydrosilylation reaction can be conducted at temperatures of from about −10° C. to about 200° C. If desired, when the hydrosilylation reaction is completed, the catalyst composition can be removed from the reaction product by filtration. The hydrosilylation can be conducted by reacting one mole of the same type silyl hydride with one mole of the same type of unsaturated compound as for the dehydrogenative silylation.

The manner or order in which the respective components for carrying out the process are added to one another is not particularly limited and can be chosen as desired. In one embodiment, the silyl hydride can be added to a mixture containing the cobalt complex and the unsaturated olefin. In another embodiment, the unsaturated olefin can be added to a mixture containing the cobalt complex and the silyl hydride. In still another embodiment, a mixture of silyl hydride and unsaturated olefin can be added to a mixture of the cobalt complex, silyl hydride and unsaturated olefin. It will be appreciated that the first mixtures in the above embodiments may be heated or preliminarily reacted prior to addition of the remaining components.

As described above, the catalyst can comprise a cobalt complex of Formula (I). In one embodiment, for a hydrosilylation process, the cobalt complex is such that $R^6$ and/or $R^7$ in Formula (I) are an alkyl group. In one embodiment, $R^6$ and $R^7$ are methyl. In one embodiment, the hydrosilylation process can employ a cobalt complex of Formula (IV), Formula (V), or a combination thereof.

The cobalt complexes of the invention are efficient and selective in catalyzing hydrosilylation reactions. For example, when the metal complexes of the invention are employed in the hydrosilylation of an alkyl-capped allyl polyether and a compound containing an unsaturated group, the reaction products are essentially free of unreacted alkyl-capped allyl polyether and its isomerization products. In one embodiment, the reaction products do not contain the unreacted alkyl-capped allyl polyether and its isomerization products. In one embodiment, the hydrosilylation process can produce some dehydrogenative silylated products. The hydrosilylation process, however, can be highly selective for the hydrosilylated product, and the products are essentially free of the dehydrogenative product. As used herein, "essentially free" is meant no more than 10 wt. %, no more than 5 wt. %, no more than 3 wt. %; even no more than 1 wt. % based on the total weight of the hydrosilylation product. "Essentially free of internal addition products" is meant that silicon is added to the terminal carbon.

The catalyst composition can be provided for either the dehydrogenative silylation or hydrosilylation reactions in an amount sufficient to provide a desired metal concentration. In one embodiment, the concentration of the catalyst is about 5% (50000 ppm) or less based on the total weight of the reaction mixture; about 1% (10000 ppm) or less; 5000 ppm or less based on the total weight of the reaction mixture; about 1000 ppm or less; about 500 ppm or less based on the total weight of the reaction mixture; about 100 ppm or less; about 50 ppm or less based on the total weight of the reaction mixture; even about 10 ppm or less based on the total weight of the reaction mixture. In one embodiment, the concentration of the catalyst is from about 10 ppm to about 50000 ppm; about 100 ppm to about 10000 ppm; about 250 ppm to about 5000 ppm; even about 500 ppm to about 2500 ppm. In one embodiment, the concentration of the metal atom is from about 100 to about 1000 ppm based on the total weight of the reaction mixture. The concentration of the metal (e.g., cobalt) can be from about 1 ppm to about 5000 ppm; from about 5 ppm to about 2500 ppm; from about 10 ppm to about 1000 ppm, even from about 25 ppm to about 500 ppm. Here as elsewhere in the specification and claims, numerical values can be combined to form new and non-disclosed ranges.

The following examples are intended to illustrate, but in no way limit the scope of the present invention. All parts and percentages are by weight and all temperatures are in Celsius unless explicitly stated otherwise. All the publications and the US patents referred to in the application are hereby incorporated by reference in their entireties.

EXAMPLES

General Considerations

All air- and moisture-sensitive manipulations were carried out using standard Schlenk techniques or in an MBraun inert atmosphere dry box containing an atmosphere of purified nitrogen. Solvents for air- and moisture-sensitive manipulations were dried and deoxygenated by passing through solvent system columns and stored with 4 Å molecular sieves in the dry box. Benzene-$d_6$ was purchased from Cambridge Isotope Laboratories, dried over sodium and stored with 4 Å molecular sieves in the dry box. Complexes ($^{Mes}$PDI)CoMe and ($^{Cy}$APDI)CoMe were prepared according to the procedure described in Humphries, M. J.; Tellmann, K. P.; Gibson, V. C.; White, A. J. P.; Williams, D. J. *Organometallics* 2005, 24, 2039-2050. Py$_2$Co(CH$_2$TMS)$_2$ was prepared according to the procedure described in Zhu, D.; Janssen, F. F. B. J.; Budzelaar, P. H. M. *Organometallics* 2010, 29, 1897.

Substrates were dried over LiAlH$_4$ or CaH$_2$ and degased under high vacuum before use.

NMR spectra were acquired on a Varian INOVA-500 or Bruker-500 MHz spectrometer. The chemical shifts (δ) of $^1$H NMR spectra are given in parts per million and referenced to the solvent residual of benzene-$d_6$ (7.16 ppm).

GC analyses were performed using a Shimadzu GC-2010 gas chromatograph equipped with a Shimadzu AOC-20s autosampler and a Shimadzu SHRXI-5MS capillary column (15 m×250 μm). The instrument was set to an injection volume of 1 μL, an inlet split ratio of 20:1, and inlet and detector temperatures of 250° C. and 275° C., respectively. UHP-grade helium was used as carrier gas with a flow rate of 1.82 mL/min. The temperature program used for all the analyses is as follows: 60° C., 1 min; 15° C./min to 250° C., 2 min.

Catalyst loadings in the following text are reported in mol % of the cobalt complex (mol$_{Co\ complex}$/mol$_{olefin}$×100).

Example 1

Synthesis of Alloxydiphenylsilane

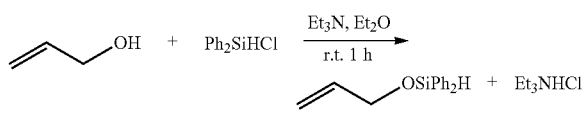

The synthesis of alloxydiphenylsilane follows a modified literature procedure described by Bergens, S. H.; Noheda, P.; Whelan, J.; Bosnich, B. *J. Am. Chem. Soc.* 1992, 114, 2121-2128, and was carried out in air. A solution of allyl alcohol (2.9 g, 50 mmol) and triethylamine (5.1 g, 50 mmol) in Et$_2$O (250 mL) was cooled in an ice bath. With rapid stirring, the solution was treated with chlorodiphenylsilane (11 g, 50 mmol) drop wise. Large quantities of a fluffy white precipitate (Et$_3$NHCl) were observed immediately. The mixture was warmed to room temperature and stirred for 1 hour. The resulting solution was filtered through Celite and washed with Et₂O. The filtrate was concentrated and yielded a colorless oil, which upon distillation (84-8 ° C., 65 mmTorr) afforded the desired product as a colorless oil in 80% yield. ¹H NMR (400 MHz, Benzene-d₆) δ 7.74-7.62 (m, 4H), 7.27-7.06 (m, 6H), 5.81 (ddt, J=17.1, 10.6, 4.6 Hz, 1H), 5.69 (s, 1H), 5.31 (dq, J=17.1, 1.8 Hz, 1H), 5.00 (dq, J=10.6, 1.8 Hz, 1H), 4.16 (dt, J=4.6, 1.8 Hz, 2H). ¹³C NMR (126 MHz, C₆D6) δ 136.73, 135.11, 134.31, 130.66, 128.39, 128.25, 128.06, 127.87, 114.77, 65.60.

Example 2

Synthesis of Alloxydimethylsilane

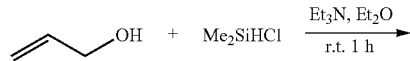

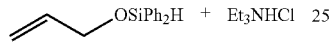

Alloxydimethylsilane was prepared in a manner similar to alloxydiphenylsilane. A solution of allyl alcohol (2.9 g, 50 mmol) and triethylamine (5.1 g, 50 mmol) in Et₂O (250 mL) was cooled in an ice bath. While rapid stirring, the solution was added with chlorodimethylsilane (4.7 g, 50 mmol) dropwise. Large quantities of a fluffy white precipitate (Et₃NHCl) were observed immediately. The mixture was warmed to room temperature and stirred for 1 h. The resulting solution was filtered through Celite and washed with Et₂O. The filtrate was concentrated to yield a colorless oil, following factional distillation (79-83° C.), afforded the product as a colorless oil in 50% yield. ¹H NMR (400 MHz, Chloroform-d) δ 5.93 (ddt, J=17.2, 10.1, 5.0 Hz, 1H), 5.26 (dq, J=17.2, 1.8 Hz, 1H), 5.12 (dq, J=10.4, 1.6 Hz, 1H), 4.68-4.55 (m, 1H), 4.18 (dt, J=5.0, 1.7 Hz, 2H), 0.23 (s, 3H), 0.23 (s, 3H).

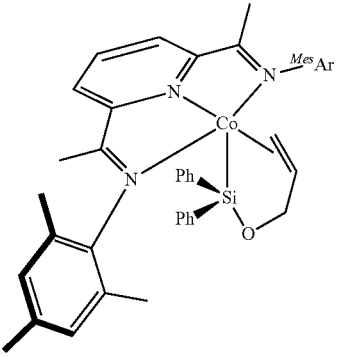

In a glove box, a purple solution of (^MesPDI)CoMe (47 mg, 0.1 mmol) in 1 mL of Et₂O and a Et₂O (1 mL) solution of alloxydiphenylsilane (24 mg, 0.1 mmol) were mixed and stirred for 0.5 hours. A maroon solution was observed. The solution was filtered through Celite and concentrated under vacuum. The resulting solution was layered with pentane and stored at −35° C. for 2 days and produced maroon crystals. ¹H NMR (400 MHz, benzene-d₆) δ 7.77 (d, J=7.6 Hz, 1H), 7.70 (d, J=7.6, 1H), 7.31 (t, J=7.6 Hz, 1H), 7.10-6.94 (m, 8 H), 6.88-6.82 (m, 2 H), 6.73-6.64 (m, 2H), 6.62 (s, 1H), 6.57 (s, 1H), 5.24 (dd, J=9.9, 5.4 Hz, 1H), 4.78 (br, 1H), 3.49 (t, J=10.4 Hz, 1H), 3.16 (d, J=8.7 Hz, 1H), 2.72 (d, J=12.5 Hz, 1H), 2.05 (s, 3H), 2.01 (s, 3H), 1.87 (s, 3H), 1.76 (s, 3H), 1.65 (s, 3H), 1.44 (s, 3H), 1.42 (s, 3H) 1.02 (s, 3H). ¹³C NMR (126 MHz, benzene-d₆) δ 154.33, 150.22, 149.42, 148.74, 147.28, 146.88, 144.56, 140.38, 137.90, 134.80, 134.69, 134.49, 133.16, 133.01, 132.25, 129.94, 129.87, 129.54, 129.33, 129.12, 129.07, 128.84, 128.57, 127.63, 127.58, 127.50, 126.34, 125.70, 122.72, 121.14, 115.77, 75.83, 71.26, 61.22, 20.81, 20.76, 20.55, 18.69, 18.04, 17.12, 15.60, 15.26.

Example 4

Synthesis of (^MeAPDI)Co(Ph₂SiOC₃H₅)

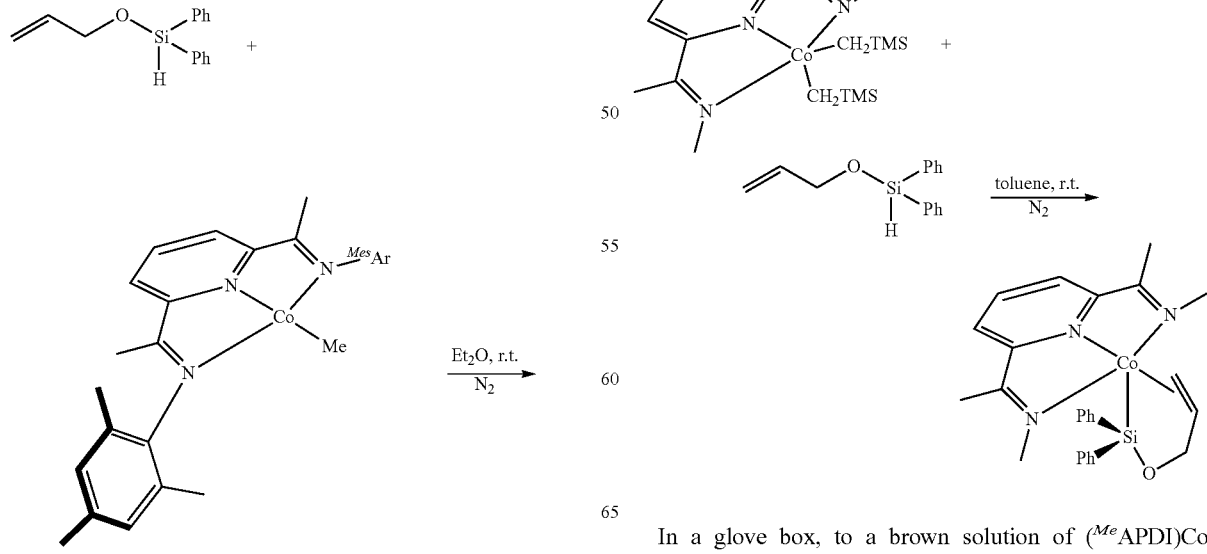

In a glove box, to a brown solution of (^MeAPDI)Co(CH₂TMS)₂ (42 mg, 0.1 mmol) in toluene was added alloxydiphenylsilane (24 mg, 0.1 mmol). The reaction mixture was stirred for 8 hours and a purple solution was observed. The solution was filtered through Celite and concentrated under vacuum. The resulting solution was layered with pentane and stored at −35° C. for 2 days to yield the desired product as purple crystals. $^1$H NMR (500 MHz, Benzene-d$_6$) δ 7.58 (d, J=7.6 Hz, 1H), 7.49 (dd, J=7.6 Hz, 1H), 7.19-6.94 (m, 7H), 6.87 (t, J=7.6 Hz, 2H), 6.56-6.50 (m, 2H), 5.43-5.36 (m, 1H), 4.32-4.22 (m, 2H), 3.35-3.29 (m, 1H), 2.89-2.91 (m, 1H), 2.39 (s, 3H), 1.83 (s, 3H), 1.62 (s, 3H), 1.40 (s, 3H). $^{13}$C NMR (126 MHz, C$_6$D$_6$) δ 152.63, 149.63, 145.92, 145.80, 144.01, 138.30, 132.15, 131.93, 128.35, 128.15, 127.97, 127.37, 127.23, 127.21, 126.83, 121.17, 119.50, 114.13, 70.81, 69.00, 47.09, 39.65, 35.26, 22.76, 14.56, 13.42.

Example 5

Synthesis of ($^{Mes}$PDI)Co(Me$_2$SiOC$_3$H$_5$)

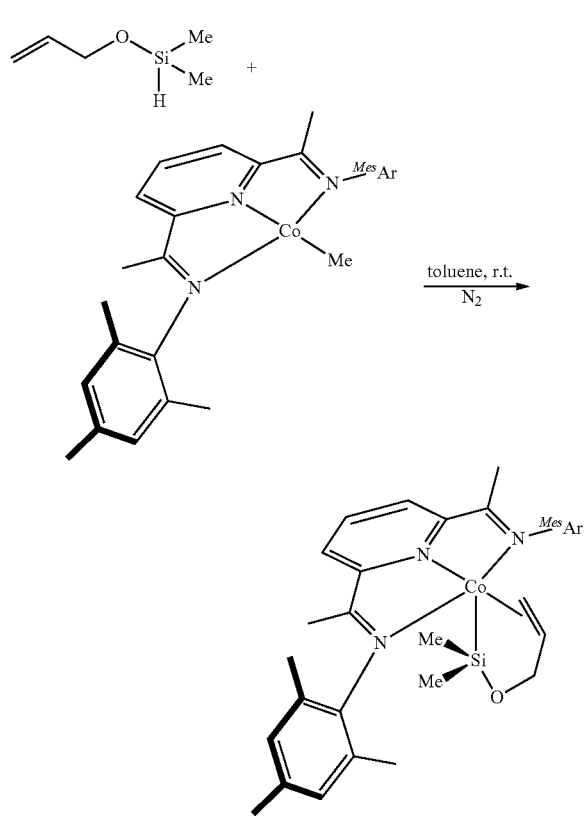

In a glove box, to a purple solution of ($^{Mes}$PDI)CoMe (47 mg, 0.1 mmol) in toluene (1 mL) was added alloxydimethylsilane (16 mg, 0.12 mmol) and stirred for 2 hours to afford a red solution. The solution was filtered through Celite and concentrated under vacuum. The resulting solution was layered with pentane and stored at −35° C. for 1 day and yielded the desired product as red crystals. $^1$H NMR (300 MHz, benzene-d$_6$) δ 7.71 (dd, J=7.6, 1.1 Hz, 1H), 7.65 (dd, J=7.7, 1.1 Hz, 1H), 7.06 (t, J=7.7 Hz, 1H), 6.76 (s, 1H), 6.70-6.65 (m, 3H), 5.05 (dd, J=9.8, 5.6 Hz, 1H), 4.90-4.75 (m, 1H), 3.30 (t, J=10.4 Hz, 1H), 3.15 (d, J=8.6 Hz, 1H), 2.65 (d, J=12.3 Hz, 1H), 2.14 (s, 3H), 2.07 (s, 6H), 2.05 (s, 3H), 1.91 (s, 6H), 1.68 (s, 3H), 1.46 (s, 3H), 1.28 (s, 3H), −0.18 (s, 3H), −0.45 (s, 3H). $^{13}$C NMR (126 MHz, benzene-d$_6$) δ 152.01, 147.97, 147.69, 147.49, 144.98, 144.56, 134.64, 134.53, 133.64, 132.68, 129.71, 129.62, 129.60, 129.45, 129.41, 129.01, 128.66, 128.35, 128.16, 127.97, 121.19, 120.85, 114.52, 76.52, 71.16, 59.70, 20.83, 20.81, 20.38, 19.91, 19.12, 18.31, 15.45, 15.44, 3.41, 1.93.

Example 6

Synthesis of ($^{Me}$APDI)Co(Me$_2$SiOC$_3$H$_5$)

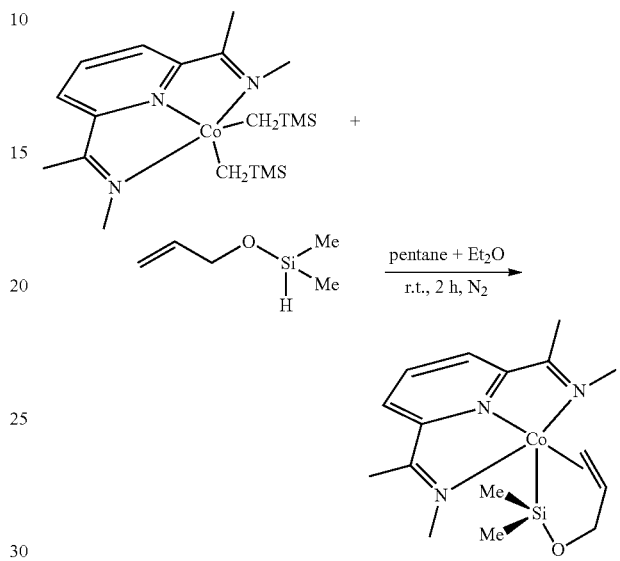

This compound was prepared in a manner similar to ($^{Mes}$PDI)Co(Me$_2$SiOC$_3$H$_5$) (Example 5). In a glove box, to a brown solution of ($^{Me}$APDI)Co(CH$_2$TMS)$_2$ (42 mg, 0.1 mmol) in pentane (1 mL) and Et$_2$O (5 drops) was added alloxydimethylsilane (16 mg, 0.12 mmol) and stirred for 6 hours. A purple solution and precipitation of solids were observed. The solid was isolated through filtration and purified by dissolving in toluene and passing through Celite. The resulting solution was layered with pentane and stored at −35° C. for 1 day to yield the desired product as purple crystals. $^1$H NMR (500 MHz, benzene-d$_6$) $^1$H NMR (300 MHz, benzene-d$_6$) δ 7.63 (dd, J=7.6, 1.1 Hz, 1H), 7.51 (dd, J=7.7, 1.2 Hz, 1H), 6.99 (t, J=7.6 Hz, 1H), 5.17 (dd, J=10.0, 6.4 Hz, 1H), 4.40-4.12 (m, 1H), 4.04 (t, J=10.2 Hz, 1H), 3.43 (dd, J=9.3, 1.3 Hz, 1H), 2.99 (dd, J=12.3, 1.3 Hz, 1H), 2.60 (s, 3H), 2.24 (s, 3H), 2.05 (s, 3H), 1.87 (s, 3H), −0.01 (s, 3H), −0.93 (s, 3H). $^{13}$C NMR (126 MHz, benzene-d$_6$) δ 151.02, 148.49, 145.32, 142.84, 120.04, 119.50, 113.29, 70.99, 68.12, 48.17, 40.03, 35.68, 14.30, 14.20, 3.80, −1.94.

Example 7

Synthesis of ($^{Me}$APDI)CoCH$_2$TMS

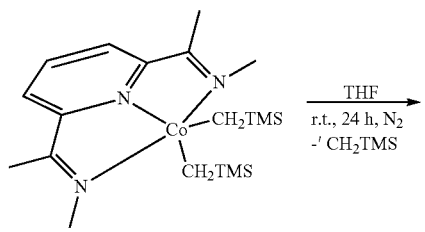

-continued

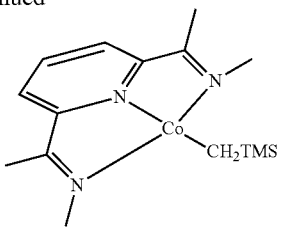

The brown solid of ($^{Me}$APDI)Co(CH$_2$TMS)$_2$ (50 mg, 0.12 mmol) was dissolved in THF (5 mL). The solution was allowed to stand in r.t. under N$_2$ for 24 h. Upon formation of ($^{Me}$APDI)Co(CH$_2$TMS), the color of the solution was changed to purple. The THF solvent was reduced to 0.5 mL and layered with 1 mL pentane. The solution was allowed to crystallize at −35° C. to afford a purple solid in 80% yield. $^1$H NMR (300 MHz, Benzene-d$_6$) δ 9.85 (t, J=7.7 Hz, 1H), 7.24 (d, J=7.7 Hz, 2H), 4.00 (s, 6H), 1.23 (s, 2H), −0.10 (s, 9H), −0.55 (s, 6H).

Example 8

Synthesis of (MeAPDI)Co(Me$_2$SiOC$_3$H$_5$)

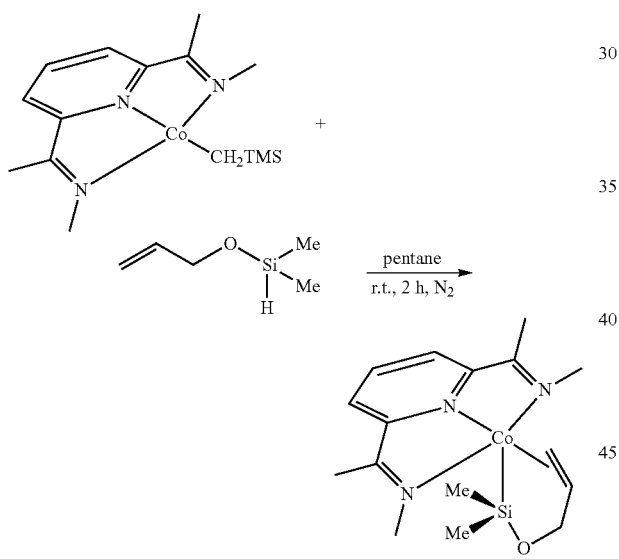

In a glove box, to a purple solution of ($^{Me}$APDI)Co(CH$_2$TMS) (200 mg, 0.60 mmol) in pentane (2 mL) was added alloxydimethylsilane (76 mg, 0.66 mmol, 1.1 equiv) and stirred for 2 hours. A precipitation of solids were observed. The solid was isolated through filtration in 92% yield. The solid is clean by $^1$H NMR spectroscopy and suitable for catalysis. If impurity is observed, the solid can be purified by recrystallization in toluene and pentane at −35° C. $^1$H NMR (500 MHz, benzene-d$_6$) $^1$H NMR (300 MHz, benzene-d$_6$) δ 7.63 (dd, J=7.6, 1.1 Hz, 1H), 7.51 (dd, J=7.7, 1.2 Hz, 1H), 6.99 (t, J=7.6 Hz, 1H), 5.17 (dd, J=10.0, 6.4 Hz, 1H), 4.40-4.12 (m, 1H), 4.04 (t, J=10.2 Hz, 1H), 3.43 (dd, J=9.3, 1.3 Hz, 1H), 2.99 (dd, J=12.3, 1.3 Hz, 1H), 2.60 (s, 3H), 2.24 (s, 3H), 2.05 (s, 3H), 1.87 (s, 3H), −0.01 (s, 3H), −0.93 (s, 3H). $^{13}$C NMR (126 MHz, benzene-d$_6$) δ 151.02, 148.49, 145.32, 142.84, 120.04, 119.50, 113.29, 70.99, 68.12, 48.17, 40.03, 35.68, 14.30, 14.20, 3.80, −1.94.

Example 9

Catalyst Screening for the Hydrosilylation 1-octene With HSi(OEt)$_3$

In a glove box, 1-octene (112 mg, 1 mmol) and triethoxysilane (164 mg, 1 mmol) were weighed into a vial equipped with a stir bar. The solid Co catalyst (2-3 mg, 0.5 mol %) was weighed into a separate vial, and was subsequently added into the substrates. The vial was sealed with a cap and stirred. After 1 hour, the reaction was quenched by exposure to air. The product mixture was filtered through silica gel and eluted with hexane. The product mixture was filtered through a plug of silica gel (Fluka® high-purity grade, pore size 60, 230-400 mesh particle size, 40-63 µm particle size, for flash chromatography) and eluted with hexane. The crude product mixture was analyzed by GC. Volatiles were then removed from the crude mixture product and the resulting mixture was analyzed by $^1$H and $^{13}$C NMR spectroscopy.

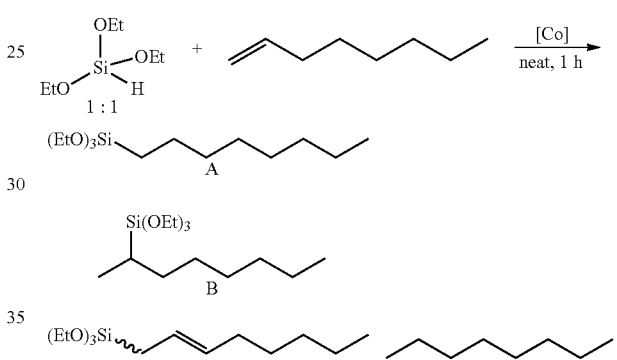

Example 10

Dehydrogenative Silylation of 1-octene With HSi(OEt)$_3$ Using ($^{Mes}$PDI)Co(Ph$_2$SiOC$_3$H$_5$) in the Glove Box

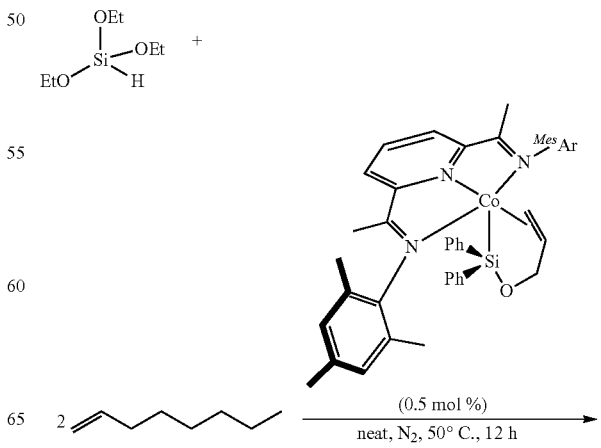

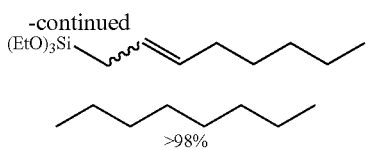

In a glove box, 1-octene (112 mg, 1 mmol) and triethoxysilane (82 mg, 0.5 mmol) were weighed into a vial equipped with a stir bar. The purple solid of ($^{Mes}$PDI)Co(Ph$_2$SiOC$_3$H$_5$) (2 mg, 0.5 mol %) was weighed into a separate vial, and was subsequently combined with the substrates. The vial was sealed with a cap and electrical tape, brought out of the box and stirred in an oil bath at 50° C. After 12 hours, the reaction was quenched by exposure to air. The product mixture was directly injected to GC. The substrates were quantitatively converted into allyl silane and octane (>98% starting olefin conversion). The residue was filtered through silica gel and eluted with hexane. The resulting solution was dried under vacuum and analyzed by $^1$H and $^{13}$C NMR spectroscopy to confirm the GC results.

Example 11

Dehydrogenative Silylation of 1-octene With HSi(OEt)$_3$ Using ($^{Mes}$PDI)Co(Me$_2$SiOC$_3$H$_5$) in the Glove Box

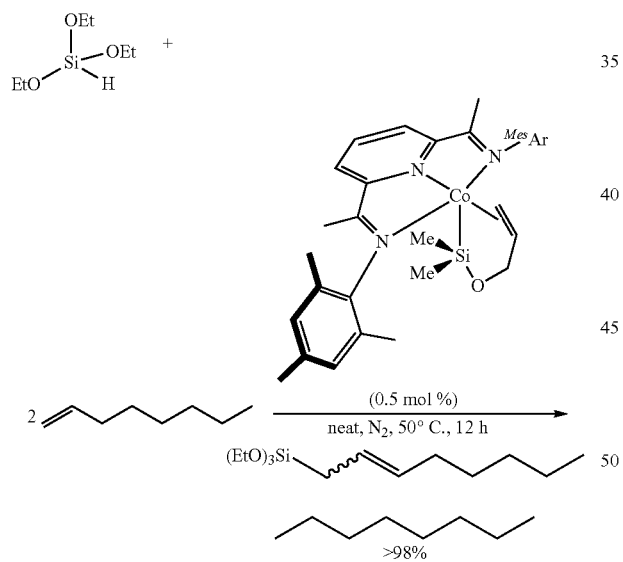

In a glove box, 1-octene (112 mg, 1 mmol) and triethoxysilane (82 mg, 0.5 mmol) were weighed into a vial equipped with a stir bar. Purple ($^{Mes}$PDI)Co(Me$_2$SiOC$_3$H$_5$) (2 mg, 0.5 mol %) was weighed into a separate vial, and was subsequently combined with the substrates. The vial was sealed with a cap and electrical tape, brought out of the box and stirred in an oil bath at 50° C. After 2 hours, the reaction was quenched by exposure to air. The product mixture was directly injected to GC. The substrates were completely converted into allyl silane and octane (>98% starting olefin conversion). The residue was filtered through silica gel and eluted with hexane. The resulting solution was dried under vacuum and analyzed by $^1$H and $^{13}$C NMR spectroscopy to confirm the GC results.

Example 12

Hydrosilylation of 1-octene With HSi(OEt)$_3$ Using ($^{Me}$APDI)Co(Ph$_2$SiOC$_3$H$_5$) in the Glove Box

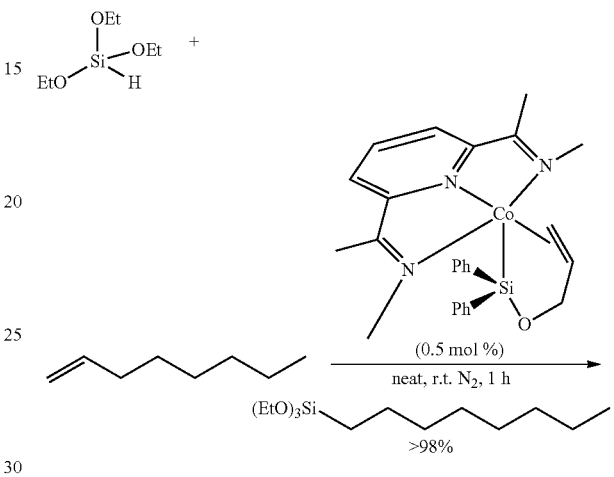

In a glove box, 1-octene (112 mg, 1 mmol) and triethoxysilane (164 mg, 1 mmol) were weighed into a vial equipped with a stir bar. Purple ($^{Me}$APDI)Co(Ph$_2$SiOC$_3$H$_5$) (2 mg, 0.5 mol %) was weighed into a separate vial, and was subsequently combined with the substrates. The mixture was stirred at r.t. for 1 hour. The reaction was quenched by exposure to air. The product mixture was directly injected to GC. The residue was filtered through silica gel and eluted with hexane. The resulting solution was dried under vacuum and analyzed by $^1$H and $^{13}$C NMR spectroscopy to confirm the GC results.

Example 13

Hydrosilylation of 1-octene with HSi(OEt)$_3$ Using ($^{Me}$APDI)Co(Me$_2$SiOC$_3$H$_5$) in the Glove Box

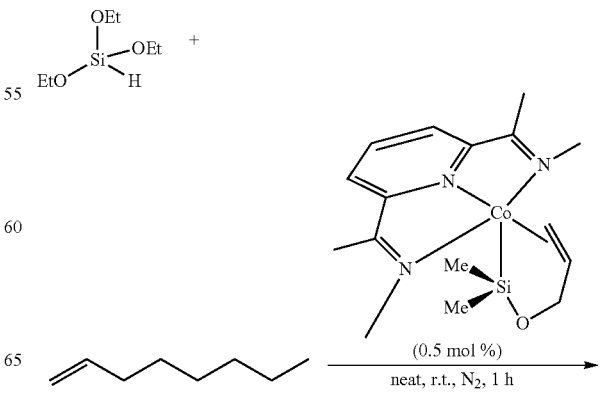

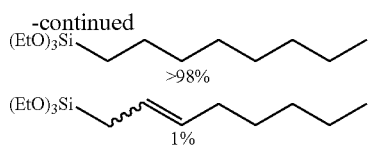

In a glove box, 1-octene (112 mg, 1 mmol) and triethoxysilane (164 mg, 1 mmol) were weighed into a vial equipped with a stir bar. Purple ($^{Me}$APDI)Co(Me$_2$SiOC$_3$H$_5$) (2 mg, 0.5 mol %) was weighed into a separate vial, and was subsequently combined with the substrates. The mixture was stirred at room temperature for 1 hour. The reaction was quenched by exposure to air. The product mixture was directly injected to GC. The residue was filtered through silica gel and eluted with hexane. The resulting solution was dried under vacuum and analyzed by $^1$H and $^{13}$C NMR spectroscopy to confirm the GC results.

Example 14

Bench-Top Dehydrogenative Silylation of 1-octene With HSi(OEt)$_3$ using ($^{Mes}$PDI)Co(Ph$_2$SiOC$_3$H$_5$) Under Ar

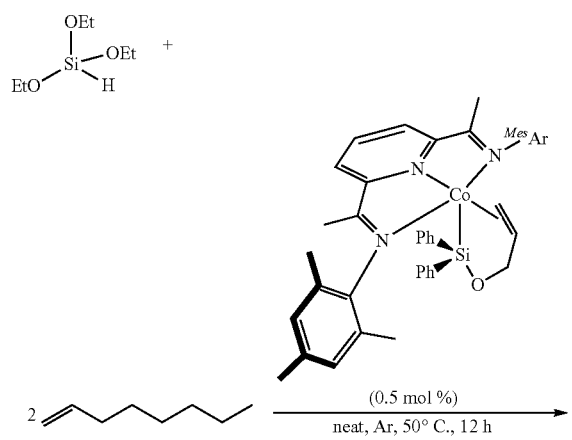

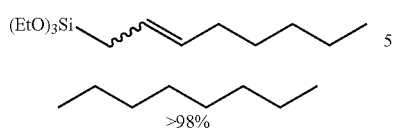

A 50 mL Schlenk flask equipped with a stir bar was charged with 1-octene (224 mg, 2 mmol) and triethoxysilane (164 mg, 1 mmol) in the glove box. The flask was sealed with a glass stopper and moved out of the box. Purple ($^{Mes}$PDI)Co (Ph$_2$SiOC$_3$H$_5$) (2 mg, 0.5 mol %) was weighed into a vial, brought out of the box and exposed to air for 10 minutes. The solid catalyst was added into the Schlenk flask under an Ar flow. The flask was sealed with a glass stopper and heated in an oil bath at 50° C. After 12 hours, the reaction was quenched by exposure to air. The reaction mixture was analyzed by GC to give complete conversion and >95% allyl silane. The residue was filtered through silica gel and eluted with hexane. The resulting solution was dried under vacuum and analyzed by $^1$H and $^{13}$C NMR spectroscopy.

Example 15

Bench-Top Hydrosilylation of 1-octene With HSi(OEt)$_3$ Using ($^{Me}$APDI)Co(Ph$_2$SiOC$_3$H$_5$) Under Ar

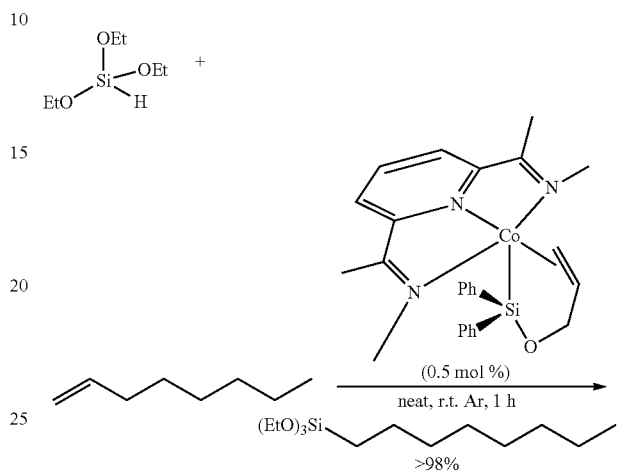

A 50 mL Schlenk flask equipped with a stir bar was charged with 1-octene (112 mg, 1 mmol) and triethoxysilane (164 mg, 1 mmol) in the glove box. The flask was sealed with a glass stopper and moved out of the box. Purple ($^{Me}$APDI)Co(Ph$_2$SiOC$_3$H$_5$) (2 mg, 0.5 mol %) was weighed into a vial, brought out of the box and exposed to air for 10 minutes. The solid catalyst was added into the Schlenk flask under an Ar flow. The flask was sealed with a glass stopper and stirred for 1 hour. The reaction was quenched by exposure to air. The reaction mixture was analyzed by GC and $^1$H NMR spectroscopy which showed >98% yield of anti-Markovnikov hydrosilylation product.

Example 16

Bench-Top Hydrosilylation of 1-octene with HSi(OEt)$_3$ Using ($^{Me}$APDI)Co(Me$_2$SiOC$_3$H$_5$) Under Ar

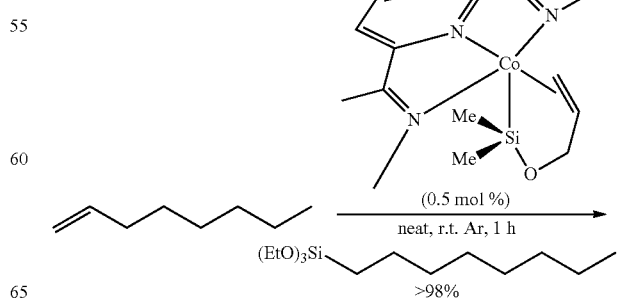

A 50 mL Schlenk flask equipped with a stir bar was charged with 1-octene (112 mg, 1 mmol) and triethoxysilane (164 mg, 1 mmol) in the glove box. The flask was sealed with a glass stopper and moved out of the box. Purple ($^{Me}$APDI)Co(Me$_2$SiOC$_3$H$_5$) (2 mg, 0.5 mol %) was weighed into a vial, brought out of the box and exposed to air for 10 minutes. The solid catalyst was added into the Schlenk flask under an Ar flow. The flask was sealed with a glass stopper and stirred for 1 hour. The reaction was quenched by exposure to air. The reaction mixture was analyzed by GC and $^1$H NMR spectroscopy which showed >98% yield of anti-Markovnikov hydrosilylation product and trace dehydrogenative silylation product.

Example 17

Bench-Top Siloxane Cross-Linking Using ($^{Me}$APDI)Co(Ph$_2$SiOC$_3$H$_5$) Under Ar

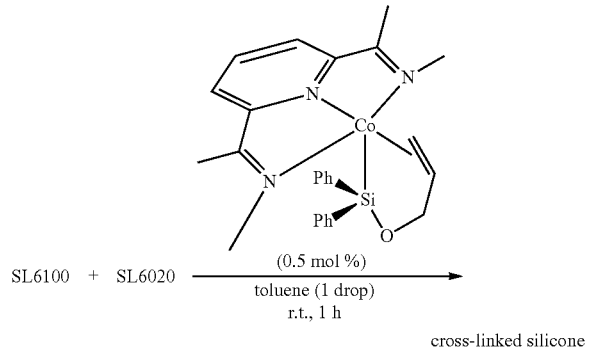

SL6100 and SL6020 were stored in air and used without further purification. A 50 mL Schlenk flask equipped with a stir bar was charged with SL6100 (1 g) and SL6020 D1 (44 mg) in air. A drop of toluene was added into the mixture. The flask was purged with Ar for 1 minute. ($^{Me}$APDI)Co(Ph$_2$SiOC$_3$H$_5$) (2 mg, 0.5 mol %) was weighed into a vial, brought out of the box and exposed to air for 5 minutes. The air-exposed solid catalyst was added into the Schlenk flask under an Ar flow. The flask was sealed with a glass stopper. During 1 h, formation of gel was observed.

Example 18

Silylation of M$^{Vi}$M$^{Vi}$ with MD$^H$M Using $^{Me}$APDICo(Me$_2$SiOAllyl)

In a nitrogen-filled drybox, a scintillation vial was charged with 0.090 g (0.483 mmol) of M$^{Vi}$M$^{Vi}$ and approximately 0.002 g (0.005 mmol) $^{Me}$APDICo(Me$_2$SiOAllyl) (1 mol %). MD$^H$M (0.215 g, 0.966 mmol) was then added to the mixture and the reaction was stirred at room temperature for 1 hour, after which the mixture was quenched by exposure to air. The product mixture was filtered through silica gel and eluted with hexane. The crude product mixture was analyzed by GC. Volatiles were then removed from the crude mixture product and the resulting mixture was analyzed by $^1$H and $^{13}$C NMR spectroscopy. The multiplets at ~0.5 ppm region (indicative of Anti-Markovnikov product) and the doublet at ~1.0 ppm region (Markovnikov product) in the $^1$H NMR spectrum are diagnostic signals for determining product ratio.

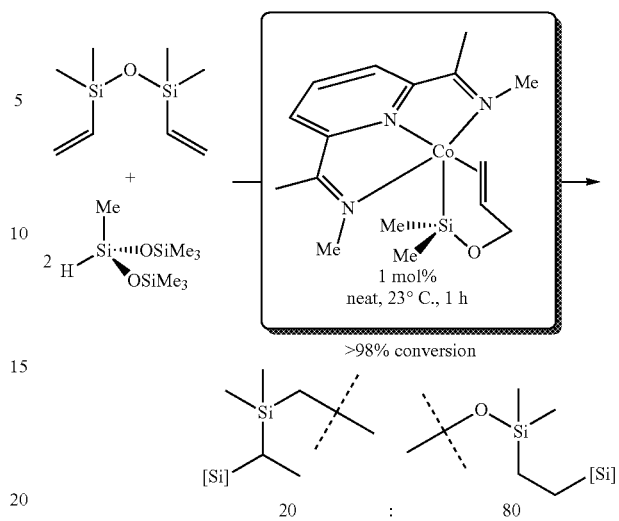

Example 19

Silylation of Vinyltrimethylsilane with MD$^H$M Using $^{Me}$APDICo(Me$_2$SiOAllyl)

In a nitrogen-filled drybox, a scintillation vial was charged with 0.090 g (0.898 mmol) of vinyltrimethylsilane and approximately 0.002 g (0.005 mmol) $^{Me}$APDICo(Me$_2$SiOAllyl) (1 mol %). MD$^H$M (0.200 g, 0.898 mmol) was then added to the mixture and the reaction was stirred at room temperature for 1 hour, after which the mixture was quenched by exposure to air. The product mixture was filtered through silica gel and eluted with hexane. The crude product mixture was analyzed by GC. Volatiles were then removed from the crude mixture product and the resulting mixture was analyzed by $^1$H and $^{13}$C NMR spectroscopy. The multiplets at ~0.5 ppm region (indicative of Anti-Markovnikov product) and the doublet at ~1.0 ppm region (Markovnikov product) in the $^1$H NMR spectrum are diagnostic signals for determining product ratio.

Example 20

Silylation of 1,1,1,3,5,5,5-heptamethyl-3-vinyltrisiloxane with pentamethyldisiloxane using $^{Me}$APDICo(Me$_2$SiOAllyl)

In a nitrogen-filled drybox, a scintillation vial was charged with 0.221 g (0.891 mmol) of 1,1,1,3,5,5,5-heptamethyl-3-vinyltrisiloxane and approximately 0.003 g (0.009 mmol) $^{Me}$APDICo(Me$_2$SiOAllyl) (1 mol %). Pentamethyldisiloxane (0.132 g, 0.891 mmol) was then added to the mixture and the reaction was stirred at room temperature for 1 hour, after which the mixture was quenched by exposure to air. The product mixture was filtered through silica gel and eluted with hexane. The crude product mixture was analyzed by GC. Volatiles were then removed from the crude mixture product and the resulting mixture was analyzed by $^1$H and $^{13}$C NMR spectroscopy. The multiplets at ~0.5 ppm region (indicative of Anti-Markovnikov product) and the doublet at ~1.0 ppm region (Markovnikov product) in the $^1$H NMR spectrum are diagnostic signals for determining product ratio.

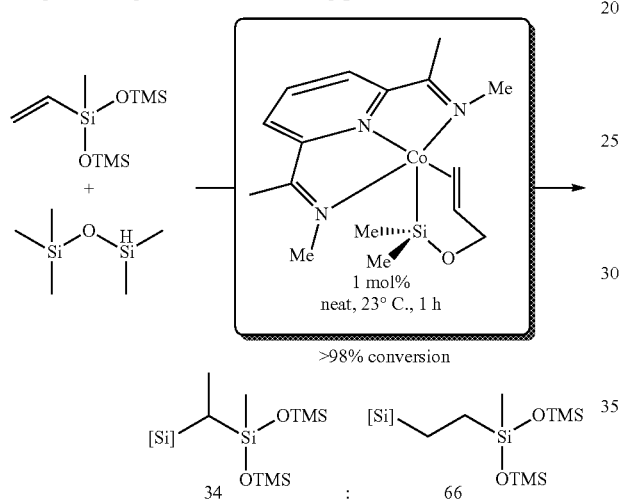

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A complex of the formula:

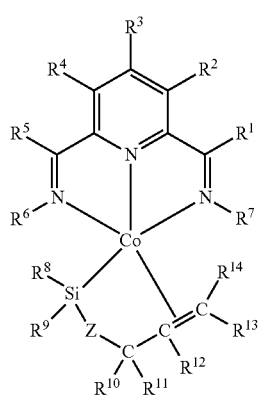

(I)

wherein each occurrence of R$^1$, R$^2$, R$^3$, R$^4$, R$^5$, R$^8$, R$^9$, R$^{10}$, R$^{11}$, R$^{12}$, R$^{13}$, and R$^{14}$ is independently hydrogen, a C1-C18 alkyl, a C1-C18 substituted alkyl, a C6-C18 aryl, a substituted C6-C18 aryl, or an inert substituent, wherein one or more of R$^1$-R$^5$ and R$^8$-R$^{14}$, other than hydrogen, optionally contain at least one heteroatom; each occurrence of R$^6$ and R$^7$ is independently a C1-C18 alkyl, a C1-C18 substituted alkyl, a C6-C18 aryl or a substituted C6-C18 aryl, wherein one or both R$^6$ and R$^7$ optionally contain at least one heteroatom; optionally any two of R$^1$, R$^2$, R$^3$, R$^4$, R$^5$, R$^6$, and R$^7$ vicinal to one another, R$^1$-R$^2$, and/or R$^4$-R$^5$ taken together may form a ring being a substituted or unsubstituted, saturated, or unsaturated cyclic structure, with the proviso that R$^5$-R$^6$ and R$^1$-R$^7$ are not taken to form a terpyridine ring; and Z is O, NR$^{15}$, or CR$^{16}$R$^{17}$, wherein R$^{15}$, R$^{16}$, and R$^{17}$ is independently hydrogen, a C1-C18 alkyl, C1-C18 substituted alkyl, a C6-C18 aryl, or a substituted C6-C18 aryl group, an alkaryl group, an aralkyl group, and one or more of R$^{15}$, R$^{16}$, and R$^{17}$ optionally contain at least one heteroatom.

2. The complex of claim 1, wherein Z is O, and R$^8$ and R$^9$ are independently chosen from a C1-C4 alkyl or a C6-C10 aryl.

3. The complex of claim 1, wherein Z is O, and R$^8$ and R$^9$ are independently chosen from methyl or phenyl.

4. The complex of claim 1, wherein R$^6$ and R$^7$ are independently chosen from a C1-C8 linear, branched, or cyclic alkyl, a C6-C18 aryl, or a substituted C6-C18 aryl.

5. The complex of claim 1, wherein R$^6$ and/or R$^7$ comprise an aryl of the formula:

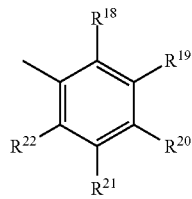

wherein each occurrence of R$^{18}$, R$^{19}$, R$^{20}$, R$^{21}$, and R$^{22}$ is independently hydrogen, a C1-C18 alkyl, a C1-C18 substituted alkyl, a C6-C18 aryl, a substituted C6-C18 aryl, or an inert substituent, wherein one or more of R$^{18}$-R$^{22}$, other than hydrogen, optionally contain at least one heteroatom.

6. The complex of claim 5, wherein R$^{18}$, R$^{20}$, and R$^{22}$ are a C1-C4 alkyl, and R$^{19}$ and R$^{21}$ are hydrogen.

7. The complex of claim 1, wherein the complex is of the formula:

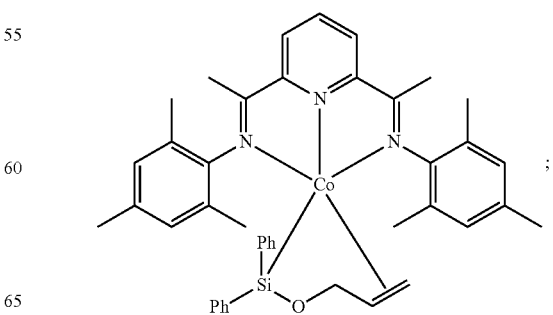

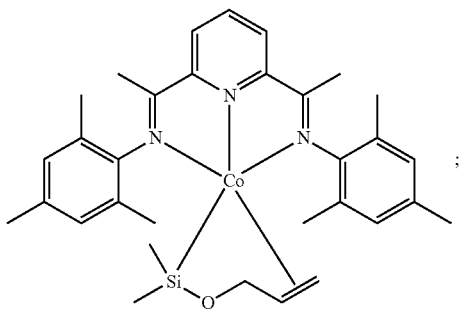

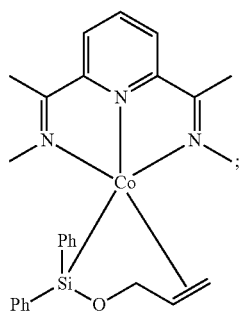

or

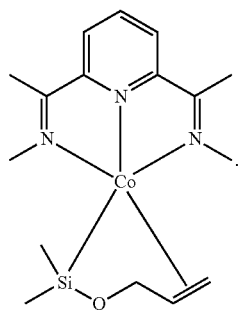

8. The complex of claim 1, wherein the complex is immobilized on a support.

9. The complex of claim 8, wherein the support is chosen from carbon, silica, alumina, MgCl$_2$, zirconia, polyethylene, polypropylene, polystyrene, poly(aminostyrene), sulfonated polystyrene, or a combination of two or more thereof.

10. The complex of claim 8, wherein at least one of $R^1$, $R^2$, $R^3$, $R^4$, $R^5$, $R^6$, and/or $R^7$ comprises a functional group that covalently bonds with the support.

11. A process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (I) or an adduct thereof:

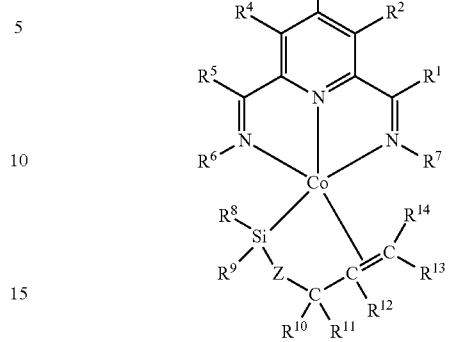

wherein each occurrence of $R^1$, $R^2$, $R^3$, $R^4$, $R^5$, $R^8$, $R^9$, $R^{10}$, $R^{11}$, $R^{12}$, $R^{13}$, and $R^{14}$ is independently hydrogen, a C1-C18 alkyl, a C1-C18 substituted alkyl, a C6-C18 aryl, a substituted C6-C18 aryl, or an inert substituent, wherein one or more of $R^1$-$R^5$ and $R^8$-$R^{14}$, other than hydrogen, optionally contain at least one heteroatom; each occurrence of $R^6$ and $R^7$ is independently a C1-C18 alkyl, a C1-C18 substituted alkyl, a C6-C18 aryl or a substituted C6-C18 aryl, wherein one or both $R^6$ and $R^7$ optionally contain at least one heteroatom; optionally any two of $R^1$, $R^2$, $R^3$, $R^4$, $R^5$, $R^6$, and $R^7$ vicinal to one another, $R^1$-$R^2$, and/or $R^4$-$R^5$ taken together may form a ring being a substituted or unsubstituted, saturated, or unsaturated cyclic structure, with the proviso that $R^5$-$R^6$ and $R^1$-$R^7$ are not taken to form a terpyridine ring; and Z is O, $NR^{15}$, or $CR^{16}R^{17}$, wherein $R^{15}$, $R^{16}$, and $R^{17}$ is independently hydrogen, a C1-C18 alkyl, C1-C18 substituted alkyl, a C6-C18 aryl, or a substituted C6-C18 aryl group, an alkaryl group, an aralkyl group, and one or more of $R^{15}$, $R^{16}$, and $R^{17}$ optionally contains at least one heteroatom.

12. The process of claim 11, wherein one or both of $R^6$ and $R^7$ comprise an aryl of the formula:

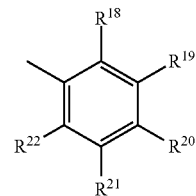

wherein each occurrence of $R^{18}$, $R^{19}$, $R^{20}$, $R^{21}$, and $R^{22}$ is independently hydrogen, a C1-C18 alkyl, a C1-C18 substituted alkyl, a C6-C18 aryl, a substituted C6-C18 aryl, or an inert substituent, wherein one or more of $R^{18}$-$R^{22}$, other than hydrogen, optionally contain at least one heteroatom.

13. The process of claim 12 wherein $R^{18}$ and $R^{22}$ are independently methyl, ethyl or isopropyl groups and $R^3$ is hydrogen or methyl.

14. The process of claim 12 wherein $R^{18}$, $R^{20}$, and $R^{22}$ are each methyl.

15. The process of claim 12 wherein $R^1$ and $R^5$ are independently methyl or phenyl groups.

16. The process of claim 12 wherein $R^2$, $R^3$, and $R^4$ are hydrogen.

17. The process of claim 11, wherein the catalyst is chosen from a complex of the formula:

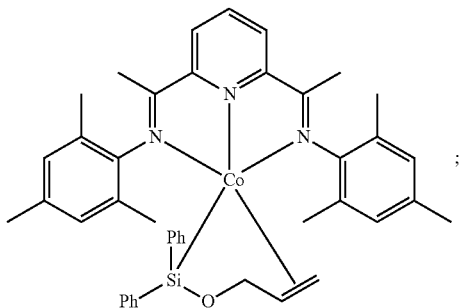

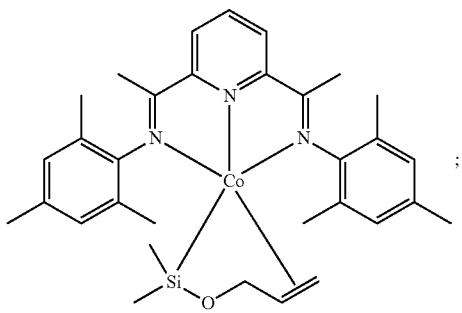

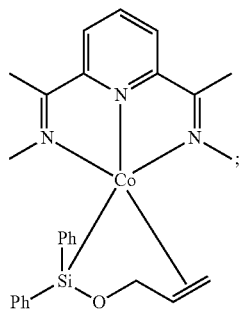

or

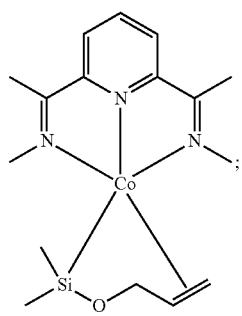

or a combination of two or more thereof.

18. The process of claim 11 further comprising removing the complex and/or derivatives thereof from the dehydrogenative silylated product.

19. The process of claim 11, wherein the dehydrogenatively silylated product comprises a silane or siloxane containing a silyl group and an unsaturated group.

20. The process of claim 19, wherein the unsaturated group is in the alpha or beta position relative to the silyl group.

21. The process of claim 11, wherein the molar ratio of the unsaturated group in said component (a) relative to the silyl-hydride functional group in said component (b) is equal to 2:1 or greater.

22. The process of claim 11, wherein the dehydrogenatively silylated product contains two or more terminal silyl groups derived from component (b).

23. The process of claim 11, wherein said component (a) is a mono-unsaturated compound.

24. The process of claim 11, wherein said component (a) is selected from the group consisting of an alkyne or an olefin; a cycloalkene; an alkyl-capped allyl polyether; a vinyl-functional alkyl-capped allyl or methallyl polyether; an alkyl-capped terminally unsaturated amine; an alkyne; terminally unsaturated acrylate or methacrylate; unsaturated aryl ether; vinyl-functionalized polymer or oligomer; vinyl-functionalized and/or terminally unsaturated alkenyl-functionalized silane and/or silicone; an unsaturated fatty acid; an unsaturated ester; or a combination of two or more thereof.

25. The process of claim 11, wherein the complex is immobilized on a support.

26. The process of claim 11, wherein the reaction is conducted under an inert atmosphere.

27. The process of claim 11, wherein the reaction is conducted in the presence of a solvent selected from the group consisting of hydrocarbons, halogenated hydrocarbons, ethers, and combinations thereof.

28. The process of claim 11, wherein the reaction is carried out at a temperature of −40° C. to 200° C.

29. The process of claim 11, wherein the silylated product comprises an anti-Markovnikov addition product, a Markovnkiov addition product, or a combination thereof.

30. A composition produced by the process of claim 11, wherein the composition contains the catalyst or derivatives thereof.

31. The composition of claim 30 comprising at least one component chosen from a silane, a silicone fluid, a crosslinked silicone, or a combination of two or more thereof.

32. A process for producing a crosslinked material, comprising reacting a mixture comprising (a) a silyl-hydride containing polymer, (b) a mono-unsaturated olefin or an unsaturated polyolefin, or combinations thereof and (c) a catalyst, optionally in the presence of a solvent, in order to produce the crosslinked material, wherein the catalyst is a complex of the Formula (I) or an adduct thereof;

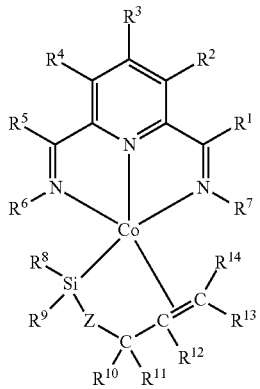

(I)

wherein each occurrence of $R^1$, $R^2$, $R^3$, $R^4$, $R^5$, $R^8$, $R^9$, $R^{10}$, $R^{11}$, $R^{12}$, $R^{13}$, and $R^{14}$ is independently hydrogen, a C1-C18 alkyl, a C1-C18 substituted alkyl, a C6-C18 aryl, a substituted C6-C18 aryl, or an inert substituent, wherein one or more of $R^1$-$R^5$, and $R^8$-$R^{14}$ other than hydrogen, optionally contain at least one heteroatom; each occurrence of $R^6$ and $R^7$ is independently a C1-C18 alkyl, a C1-C18 substituted alkyl, a C6-C18 aryl or a substituted C6-C18 aryl, wherein one or both $R^6$ and $R^7$ optionally contain at least one heteroatom; optionally any two of $R^1$, $R^2$, $R^3$, $R^4$, $R^5$, $R^6$, and $R^7$ vicinal to one another, $R^1$-$R^2$, and/or $R^4$-$R^5$ taken together may form a ring being a substituted or unsubstituted, saturated, or unsaturated cyclic structure, with the proviso that $R^5$-$R^6$ and $R^1$-$R^7$ are not taken to form a terpyridine ring; and Z is O, $NR^{15}$, or $CR^{16}R^{17}$, wherein $R^{15}$, $R^{16}$, and $R^{17}$ is independently hydrogen, a C1-C18 alkyl, C1-C18 substituted alkyl, a C6-C18 aryl, or a substituted C6-C18 aryl group, an alkaryl group, an aralkyl group, and one or more of $R^{15}$, $R^{16}$, and $R^{17}$ optionally contains at least one heteroatom.

33. A process for the hydrosilylation of a composition comprising hydrosilylation reactants chosen from (a) an unsaturated compound containing at least one unsaturated functional group, and (b) a silyl hydride containing at least one silylhydride functional group, the process comprising contacting the composition comprising the hydrosilylation reactants with a complex of the formula:

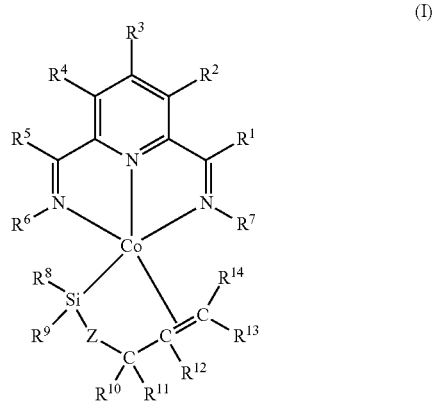

(I)

wherein each occurrence of $R^1$, $R^2$, $R^3$, $R^4$, $R^5$, $R^8$, $R^9$, $R^{10}$, $R^{11}$, $R^{12}$, $R^{13}$, and $R^{14}$ is independently hydrogen, a C1-C18 alkyl, a C1-C18 substituted alkyl, a C6-C18 aryl, a substituted C6-C18 aryl, or an inert substituent, wherein one or more of $R^1$-$R^5$, and $R^8$-$R^{14}$ other than hydrogen, optionally contain at least one heteroatom; each occurrence of $R^6$ and $R^7$ is independently a C1-C18 alkyl, a C1-C18 substituted alkyl, a C6-C18 aryl or a substituted C6-C18 aryl, wherein one or both of $R^6$ and $R^7$ optionally contain at least one heteroatom; optionally any two of $R^1$, $R^2$, $R^3$, $R^4$, $R^5$, $R^6$, and $R^7$ vicinal to one another, $R^1$-$R^2$, and/or $R^4$-$R^5$ taken together may form a ring being a substituted or unsubstituted, saturated, or unsaturated cyclic structure with the proviso that $R^5$-$R^6$ and $R^1$-$R^7$ are not taken to form a terpyridine ring; and Z is O, $NR^{15}$, or $CR^{16}R^{17}$, wherein $R^{15}$, $R^{16}$, and $R^{17}$ is independently hydrogen, a C1-C18 alkyl, C1-C18 substituted alkyl, a C6-C18 aryl, or a substituted C6-C18 aryl group, an alkaryl group, an aralkyl group, and one or more of $R^{15}$, $R^{16}$, and $R^{17}$ optionally contains at least one heteroatom.

34. The process of claim 33, wherein Z is O, and $R^8$ and $R^9$ are independently chosen from a C1-C8 alkyl and C6-C18 aryl.

35. The process of claim 33, wherein Z is O, and $R^8$ and $R^9$ are independently chosen from methyl or phenyl.

36. The process of claim 33, wherein $R^6$ and $R^7$ are independently chosen from a C1-C8 linear, branched, or cyclic alkyl, a C6-C18 aryl, or a substituted C6-C18 aryl.

37. The process of claim 33, wherein $R^6$ and $R^7$ are each methyl.

38. The process of claim 37, wherein $R^2$, $R^3$, and $R^4$ are each hydrogen.

39. The process of claim 37, wherein $R^1$ and $R^5$ are each methyl.

40. The process of claim 33, wherein the complex is of the formula:

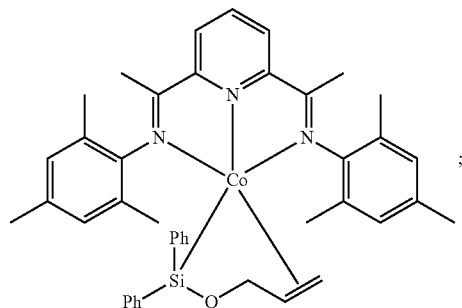

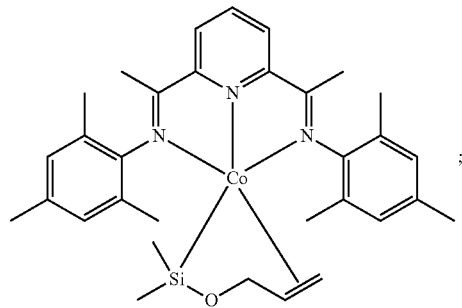

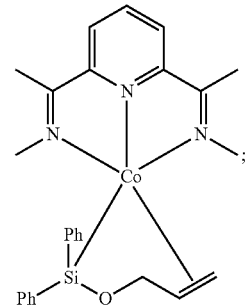

or

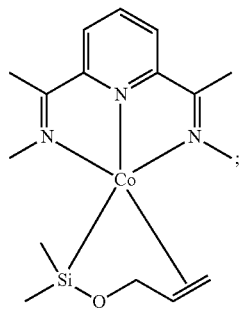

or a combination thereof.

41. The process of claim 33, wherein the complex is immobilized on a support.

42. The process according to claim 33, wherein the silyl hydride is chosen from one or a combination of compounds of the formulas:

$$R^{23}{}_mSiH_pX_{4-(m+p)};$$

$$M_aM^H{}_bD_cD^H{}_dT_eT^H{}_fQ_g;$$

$$R^{29}{}_3Si(CH_2R^{29})_xSiOSiR^{29}{}_2(OSiR^{29}{}_2)_yOSiR^{29}{}_2H;$$

$$R^{29}{}_3Si(CHR^{29})_xSiR^{29}{}_2H,$$

or a combination of two or more thereof, where each $R^{23}$ is independently a substituted or unsubstituted aliphatic or aromatic hydrocarbyl group; X is halogen, alkoxy, acyloxy, or silazane; m is 0-3; p is 1-3 with the proviso that the silicon remains tetravalent; M represents a monofunctional group of formula $R^{24}{}_3SiO_{1/2}$; a D represents a difunctional group of formula $R^{24}{}_2SiO_{2/2}$; a T represents a trifunctional group of formula $R^{24}SiO_{3/2}$; Q represents a tetrafunctional group of formula $SiO_{4/2}$; $M^H$ represents $HR^{24}{}_2SiO_{1/2}$, $T^H$ represents $HSiO_{3/2}$, and $D^H$ group represents $R^{24}HSiO_{2/2}$; each occurrence of $R^{24}$ is independently a $C_1$-$C_{18}$ alkyl, a $C_1$-$C_{18}$ substituted alkyl, a $C_6$-$C_{14}$ aryl or substituted aryl, wherein $R^{24}$ optionally contains at least one heteroatom; subscripts a, b, c, d, e, f, and g are such that the molar mass of the compound is between 100 and 100,000 Dalton; each occurrence of $R^{29}$ is independently C1-C18 alkyl, C1-C18 substituted alkyl, C6-C14 aryl or substituted aryl; x is 1-8, and y is 0-10.

43. The process according to claim 33, wherein the unsaturated compound (a) is chosen from an unsaturated polyether; a vinyl functionalized alkyl capped allyl or methylallyl polyether; a terminally unsaturated amine; an alkyne; a C2-C45 olefins; an unsaturated epoxide; a terminally unsaturated acrylate or methyl acrylate; an unsaturated aryl ether; an unsaturated aromatic hydrocarbon; unsaturated cycloalkane; a vinyl-functionalized polymer or oligomer; a vinyl-functionalized silane, a vinyl-functionalized silicone, terminally unsaturated alkenyl-functionalized silane and/or silicone or a combination of two or more thereof.

44. The process according to claim 43, wherein the unsaturated compound (a) is chosen from one or more polyethers having the general formula:

$$R^{25}(OCH_2CH_2)_z(OCH_2CHR^{27})_w\text{—}OR^{26};$$

and/or $$R^{26}O(CHR^{27}CH_2O)_w(CH_2CH_2O)_z\text{—}CR^{28}{}_2\text{—}C\text{=}C\text{—}CR^{28}{}_2(OCH_2CH_2)_z(OCH_2CHR^{27})_wR^{26}$$

wherein $R^{25}$ is chosen from an unsaturated organic group having from 2 to 10 carbon atoms; $R^{26}$ is independently chosen from a hydrogen, vinyl, allyl, methallyl, or a polyether capping group of from 1 to 8 carbon atoms, an acyl group, a beta-ketoester group, or a trialkylsilyl group; $R^{27}$ and $R^{28}$ are independently chosen from hydrogen, a monovalent hydrocarbon group, an aryl group, an alkaryl group, and a cycloalkyl group; a Me or H are preferred for $R^{27}$; each occurrence of z is 0 to 100 inclusive; and each occurrence of w is 0 to 100 inclusive.

45. The process of claim 33 further comprising removal of the catalyst composition.

46. The process of claim 45, wherein removal of the catalyst composition is achieved by filtration.

47. The process of claim 33 wherein the reaction is conducted at a temperature of from about −10° C. to about 200° C.

48. The process of claim 33, wherein the reaction is conducted a subatmospheric pressure.

49. The process of claim 33, wherein the reaction is conducted in a supra-atmospheric pressure.

* * * * *